(12) United States Patent
Perez et al.

(10) Patent No.: US 12,310,640 B2
(45) Date of Patent: May 27, 2025

(54) BONE FIXATION DEVICES, SYSTEMS, KITS, AND METHODS

(71) Applicant: GLW, Inc., Englewood Cliffs, NJ (US)

(72) Inventors: Arley Perez, Wayne, NJ (US); Garret Mauldin, Erie, CO (US); Axel Cremer, Fahrenkrug (DE)

(73) Assignee: GLW, Inc., Englewood Cliffs, NJ (US)

( * ) Notice: Subject to any disclaimer, the term of this patent is extended or adjusted under 35 U.S.C. 154(b) by 393 days.

(21) Appl. No.: 17/714,422

(22) Filed: Apr. 6, 2022

(65) Prior Publication Data

US 2022/0313327 A1    Oct. 6, 2022

Related U.S. Application Data

(60) Provisional application No. 63/171,347, filed on Apr. 6, 2021.

(51) Int. Cl.
*A61B 17/84* (2006.01)
*A61B 17/17* (2006.01)
(Continued)

(52) U.S. Cl.
CPC ........ *A61B 17/848* (2013.01); *A61B 17/1728* (2013.01); *A61B 17/808* (2013.01);
(Continued)

(58) Field of Classification Search
CPC ............ A61B 17/1604; A61B 17/1728; A61B 17/808; A61B 17/846; A61B 17/848; A61B 17/86; A61B 17/8897; A61B 17/90
See application file for complete search history.

(56) References Cited

U.S. PATENT DOCUMENTS

| 6,719,758 B2 | 4/2004 | Beger et al. |
| 7,840,254 B2 | 11/2010 | Glossop |

(Continued)

FOREIGN PATENT DOCUMENTS

| CN | 107645937 A | 1/2018 |
| EP | 2129311 B1 | 4/2012 |

(Continued)

OTHER PUBLICATIONS

International Search Report and Written Opinion, Application No. PCT/US2022/023618, dated Aug. 19, 2022.

*Primary Examiner* — Larry E Waggle, Jr.
(74) *Attorney, Agent, or Firm* — MacMillan, Sobanski & Todd, LLC

(57) ABSTRACT

Various temporary fixation devices, fixation systems and kits, and methods of fixing a bone plate to a bone are described. A temporary fixation device includes a wire member and a retaining member. The wire member has a proximal end, a distal end, a flange disposed between the proximal end and the distal end, a first portion extending from the proximal end to the flange and defining a first outer diameter, and a second portion extending from the distal end toward the flange and defining a second outer diameter and a second portion outer surface. The retaining member defines an inner passageway and can be disposed on the second portion of the wire member such that the retaining member is movable along the second portion of the wire member, from the distal end to the flange. The elongate member comprises a first material and the stopping member comprises a second material that is different from the first material.

7 Claims, 24 Drawing Sheets

(51) Int. Cl.
*A61B 17/80* (2006.01)
*A61B 17/86* (2006.01)
*A61B 17/88* (2006.01)

(52) U.S. Cl.
CPC ........ *A61B 17/863* (2013.01); *A61B 17/8897* (2013.01); *A61B 2017/8655* (2013.01)

(56) References Cited

U.S. PATENT DOCUMENTS

| | | | |
|---|---|---|---|
| 8,496,665 B2 * | 7/2013 | Cavallazzi | A61B 17/808 |
| | | | 408/241 B |
| 8,979,889 B2 | 3/2015 | Geist et al. | |
| 9,089,378 B2 | 7/2015 | Riemer et al. | |
| 9,549,771 B1 | 1/2017 | Yu et al. | |
| 9,649,138 B2 | 5/2017 | Altarae et al. | |
| 9,750,551 B1 | 9/2017 | Nichols | |
| 10,136,929 B2 | 11/2018 | Fallin et al. | |
| 2004/0097941 A1 | 5/2004 | Weiner et al. | |
| 2011/0046632 A1 | 2/2011 | Quevedo | |
| 2011/0066194 A1 | 3/2011 | Deffenbaugh et al. | |
| 2014/0074102 A1 | 3/2014 | Mandeen et al. | |
| 2015/0018835 A1 * | 1/2015 | Shea | A61B 17/1764 |
| | | | 606/96 |
| 2015/0100077 A1 * | 4/2015 | Geist | A61B 17/1757 |
| | | | 606/185 |
| 2015/0327975 A1 | 11/2015 | Euteneuer et al. | |
| 2017/0319251 A1 | 11/2017 | Viart et al. | |
| 2018/0132920 A1 | 5/2018 | Vikinsky et al. | |
| 2020/0015870 A1 * | 1/2020 | Treace | A61B 17/1604 |
| 2020/0155728 A1 * | 5/2020 | Brunelle | A61B 17/32 |

FOREIGN PATENT DOCUMENTS

| | | |
|---|---|---|
| EP | 2730245 A1 | 5/2014 |
| EP | 2731521 B1 | 7/2018 |
| EP | 3795098 A1 | 3/2021 |
| KR | 20200090542 A1 | 7/2020 |
| WO | 2008060825 A2 | 5/2008 |
| WO | 2011031495 A2 | 3/2011 |
| WO | 2016080922 A1 | 5/2016 |
| WO | 2016080923 A1 | 5/2016 |
| WO | 2016144272 A1 | 9/2016 |

* cited by examiner

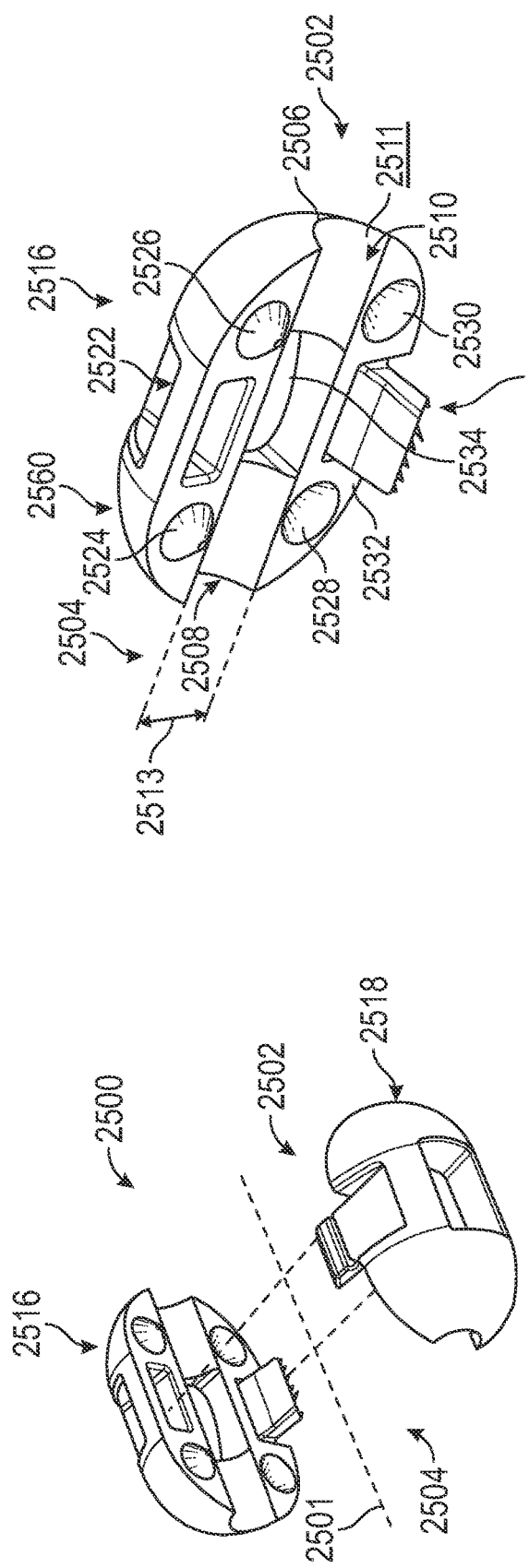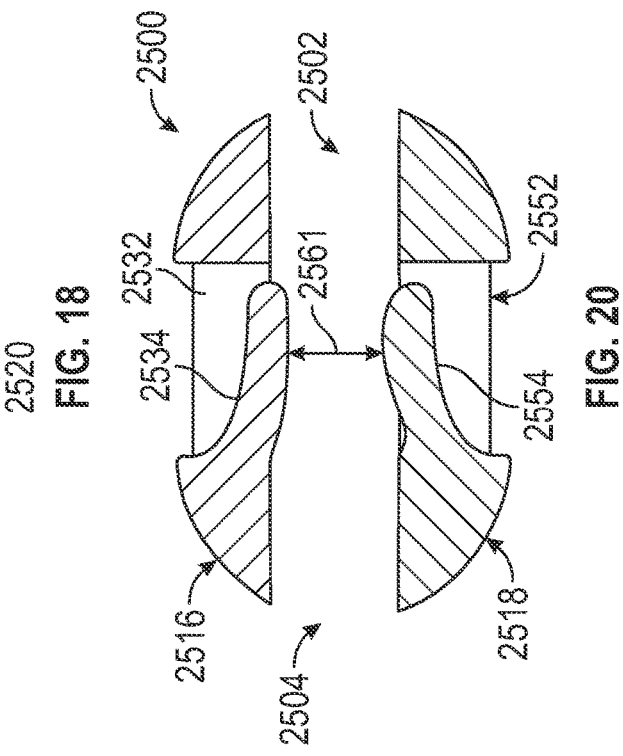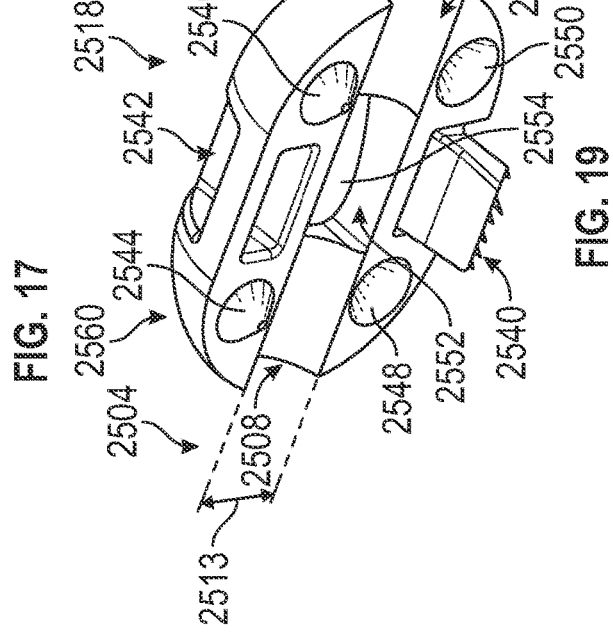

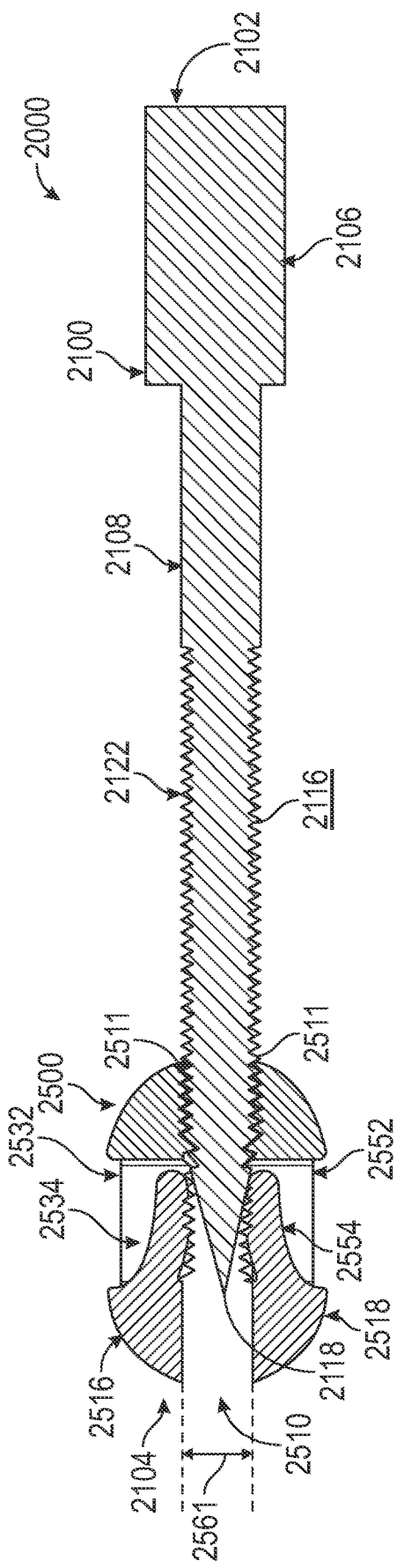
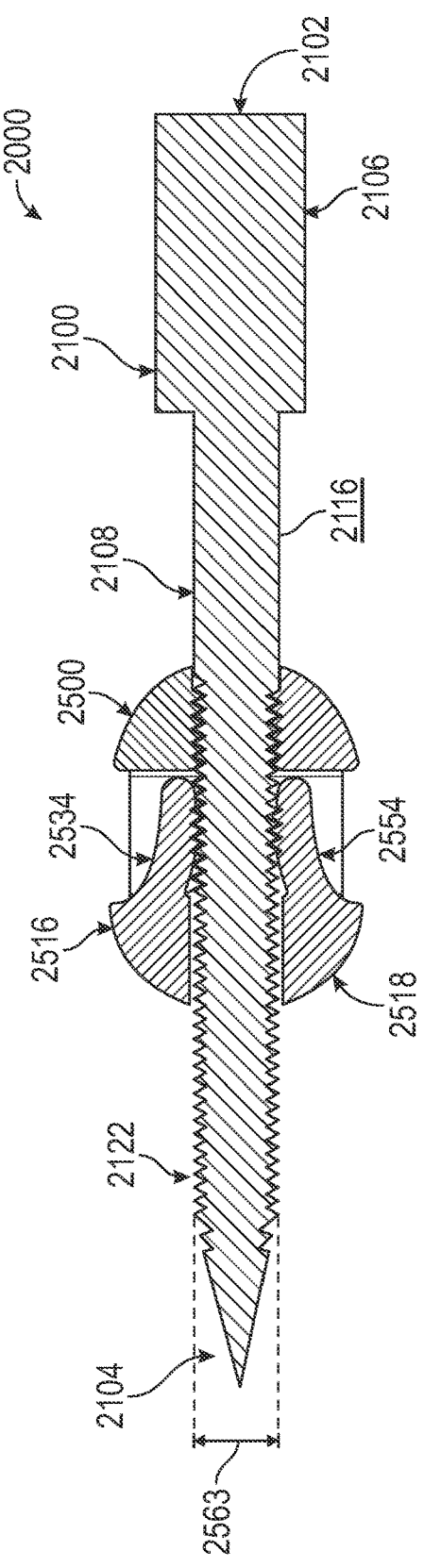
FIG. 21
FIG. 22

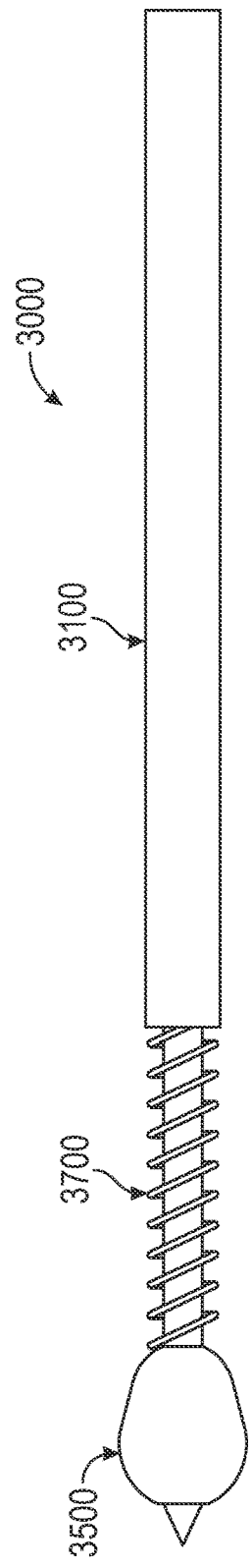
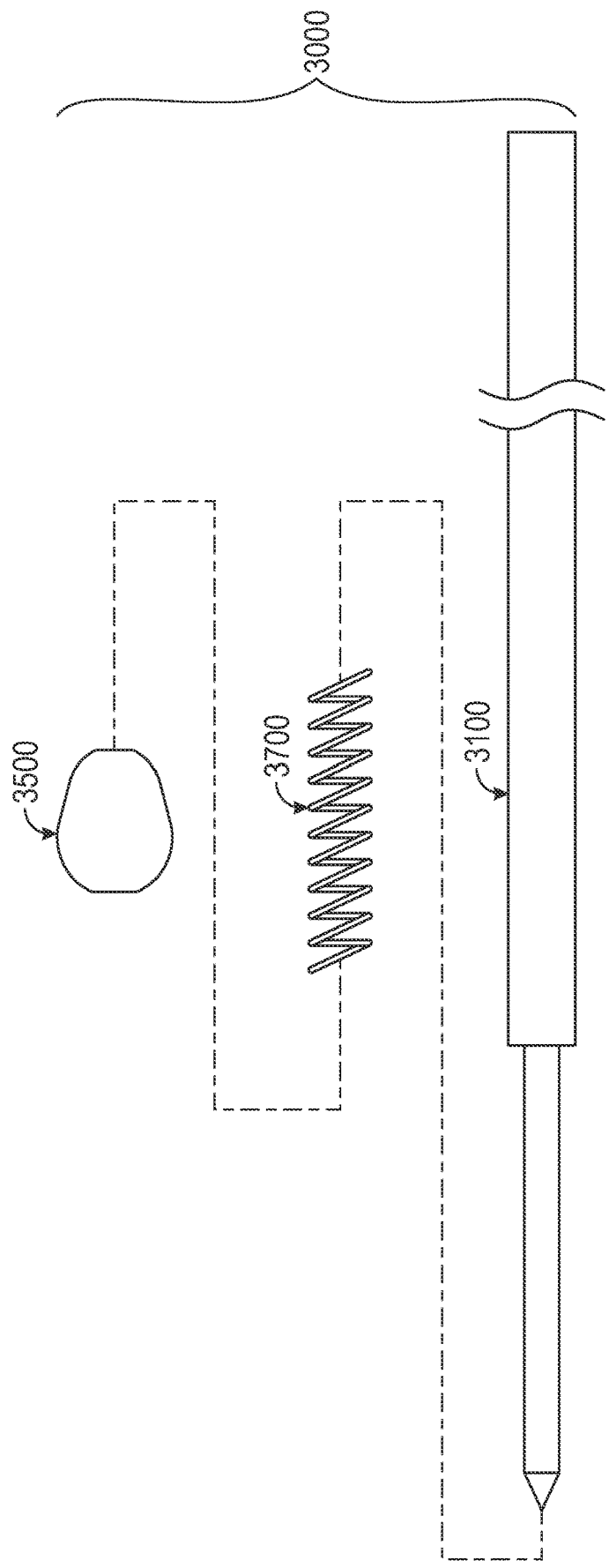
FIG. 23
FIG. 24

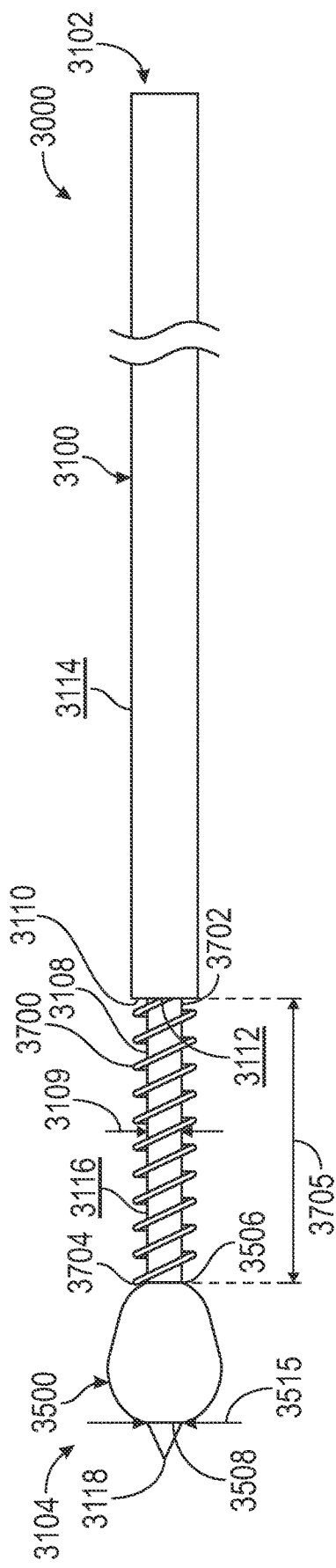
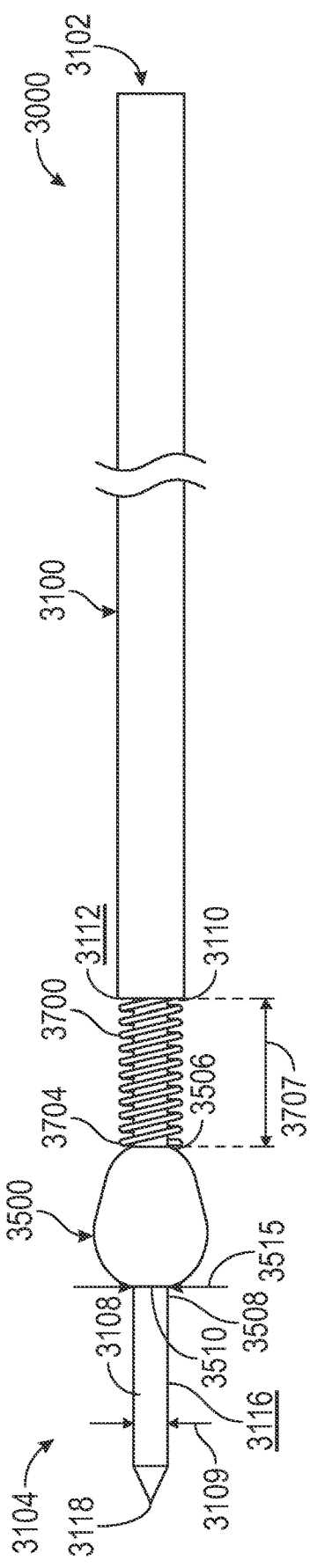
FIG. 28
FIG. 29

BONE FIXATION DEVICES, SYSTEMS, KITS, AND METHODS

RELATED APPLICATIONS

This application claims priority to U.S. Provisional Application No. 63/171,347, filed Apr. 6, 2021. The entire contents of this related application are hereby incorporated by reference into this disclosure.

FIELD

The disclosure relates to the field of medical devices. More particularly, the disclosure relates to the field of orthopedic medical devices. Specific examples relate to temporary fixation devices. The disclosure also relates to fixation systems and kits, and methods of fixing a bone plate to a bone.

BACKGROUND

Various bone fixation wires (sometimes referred to as "K-wires" or "Kirschner wires" or olive wires) for use during orthopedic and related procedures are known in the art. For example, some conventional bone fixation wires define a structural feature that interacts with orthopedic plates to prevent the wire from passing too far into the opening of the plate (sometimes referred to the olive portion of the bone fixation wire). These conventional wires have several drawbacks, however. For example, these wires are typically machined from rod stock of a single material, which creates significant waste in the manufacturing process, limits the relative geometries of the rod and bead portions of the wires, and produces bone fixation wires with undesirable balance and handling characteristics. Furthermore, the monolithic nature of conventional wires limits the effectiveness of these wires in temporarily retaining bone plates in a desired position during placement, which can result in undesirable shifting during final fixation, such as during insertion of bone screws.

A need exists, therefore, for improved temporary fixation devices, fixation systems and kits, and methods of fixing a plate to a bone.

BRIEF SUMMARY OF SELECTED EXAMPLES

An example temporary fixation device includes a wire member having a proximal end, a distal end, a flange disposed between the proximal end and the distal end, a first portion extending from the proximal end to the flange and defining a first outer diameter, and a second portion extending from the distal end toward the flange and defining a second outer diameter and a second portion outer surface, the first outer diameter being greater than the second outer diameter; and a retaining member having an inner surface that defines an inner passageway having a passageway diameter that is less than the first outer diameter, the retaining member movably disposed on the second portion of the wire member.

Another example temporary fixation device includes a wire member having a proximal end, a distal end, a flange disposed between the proximal end and the distal end, a first portion extending from the proximal end to the flange and defining a first outer diameter, and a second portion extending from the distal end toward the flange and defining a second outer diameter and a second portion outer surface; a retaining member defining an inner passageway having a first inner diameter larger than the first outer diameter of the wire member and a second inner diameter larger than the second outer diameter of the wire member, the retaining member movably disposed on the second portion of the wire member; and a spring member disposed between the flange and the retaining member and secured to the retaining member. The retaining member is movable from a first position on the second portion toward the flange to a second position on the second portion; and the spring member is biased to move the retaining member from the second position to the first position.

Another example temporary fixation device includes a wire member having a proximal end, a distal end, a flange disposed between the proximal end and the distal end, a first portion extending from the proximal end to the flange and defining a first outer diameter, and a second portion extending from the distal end toward the flange and defining a second outer diameter and a second portion outer surface that comprises a continuous and smooth surface; a retaining member defining an inner passageway having a first inner diameter larger than the first outer diameter of the wire member and a second inner diameter larger than the second outer diameter of the wire member, the retaining member movably disposed on the second portion of the wire member; and a spring member disposed between the flange and the retaining member and secured to the retaining member. The retaining member is movable from a first position on the second portion toward the flange to a second position on the second portion. The spring member is biased to move the retaining member from the second position to the first position. The wire member comprises a metal or a metal alloy. The retaining member comprises a resilient material and defines first and second arms that extend into the inner passageway and cooperatively engage the second portion outer surface.

DESCRIPTION OF FIGURES

FIG. 17 is an exploded view of the retaining member of the temporary fixation device illustrated in FIG. 14.

FIG. 18 is a perspective view of the retaining member first portion of the retaining member illustrated in FIG. 17.

FIG. 19 is a perspective view of the retaining member second portion of the retaining member illustrated in FIG. 17.

FIG. 20 is a cross-sectional view of the retaining member of the temporary fixation device illustrated in FIG. 14.

FIG. 21 is a partial cross-sectional view of the temporary fixation device illustrated in FIG. 14. The temporary fixation device is shown in the first configuration.

FIG. 22 is a partial cross-sectional view of the temporary fixation device illustrated in FIG. 14. The temporary fixation device is shown in the second configuration.

FIG. 23 is a partial side view of another example temporary fixation device.

FIG. 24 is an exploded view of the temporary fixation device illustrated in FIG. 23.

FIG. 28 is a side view of the temporary fixation device illustrated in FIG. 23. The temporary fixation device is shown in the first configuration.

FIG. 29 is a side view of the temporary fixation device illustrated in FIG. 23. The temporary fixation device is shown in the second configuration.

DETAILED DESCRIPTION OF SELECTED EXAMPLES

The following detailed description and the appended drawings describe and illustrate various example temporary fixation devices, fixation systems, fixation kits, and methods of fixing a bone plate to a bone. The description and drawings are provided to enable one skilled in the art to make and use an example temporary fixation device in accordance with the invention, to make and use an example fixation system, to make and use an example fixation kit, and to perform an example method in accordance with the invention. They are not intended to limit the scope of the claims in any manner.

The term "circumferential," and grammatically related terms, refers to a structural arrangement of one structure relative to another structure, feature, or property of another structure. The term does not require any specific dimensions, relative dimensions, configuration, or regularity of either structure.

FIGS. 1 through 6 illustrate an example temporary fixation device 1000. The temporary fixation device 1000 comprises a wire member 1100 and a retaining member 1500.

Figure 1:
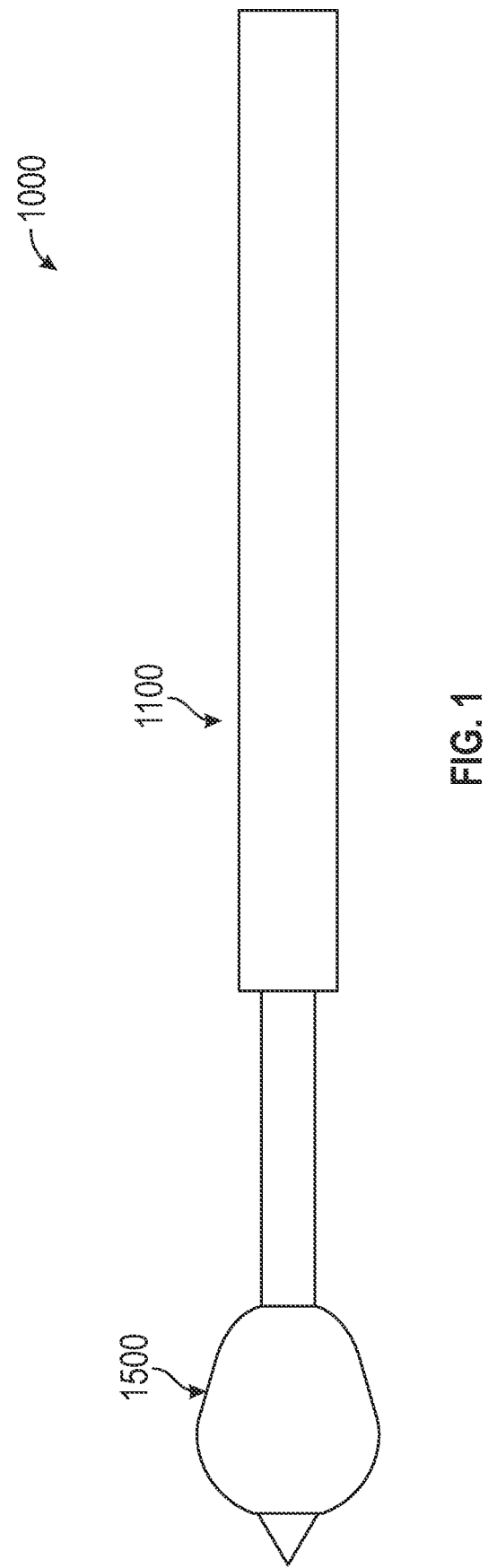
FIG. 1 is a partial side view of an example temporary fixation device.
Figure 2:
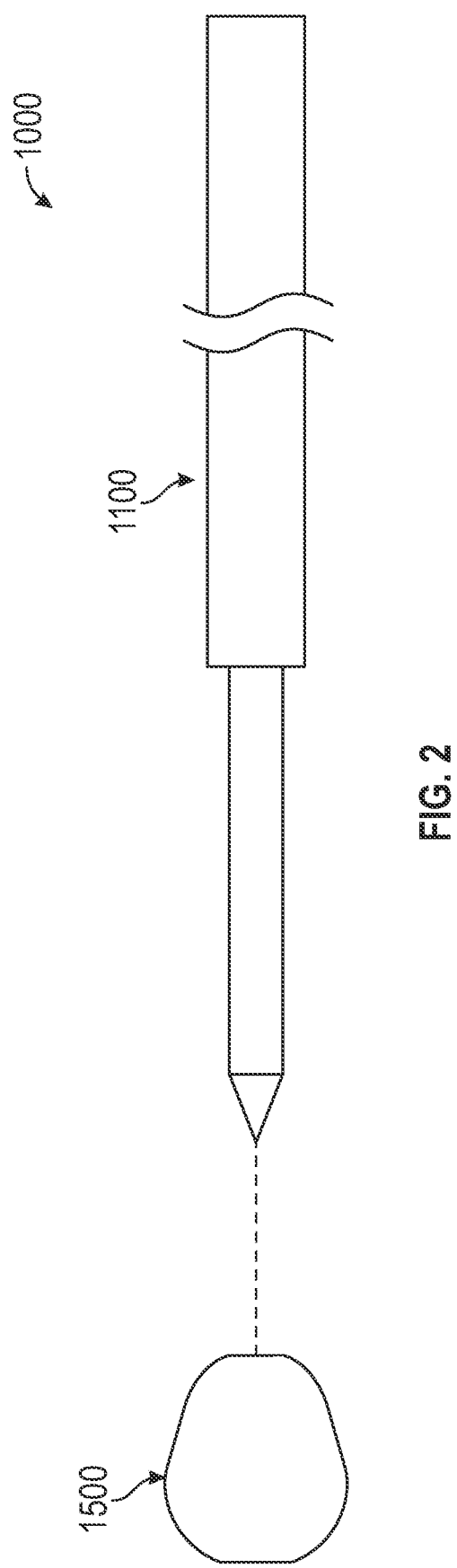
FIG. 2 is an exploded view of the temporary fixation device illustrated in FIG. 1.
Figure 3:
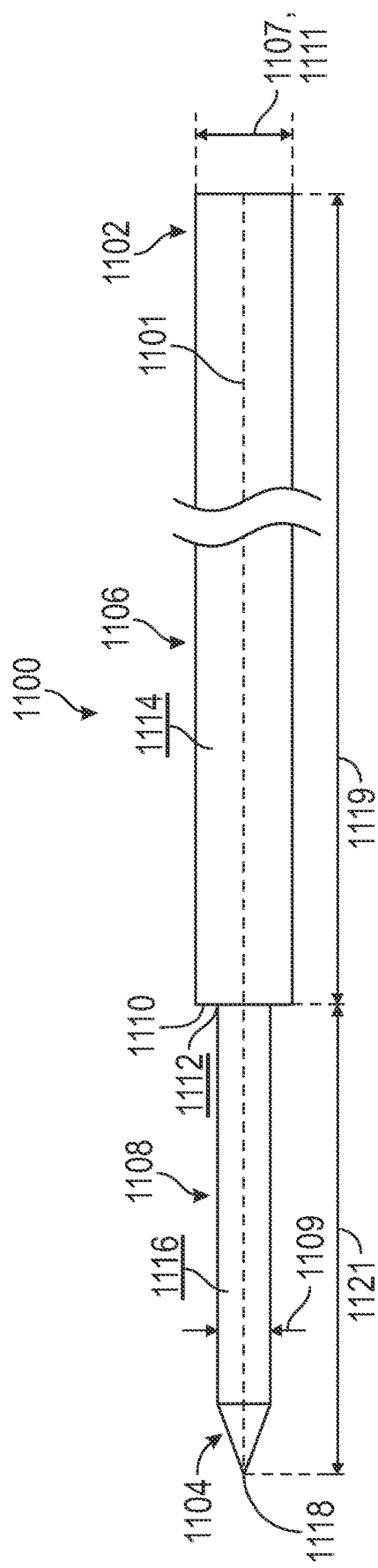
FIG. 3 is a side view of the wire member of the temporary fixation device illustrated in FIG. 2.

As illustrated in FIG. 3, the wire member 1100 has a wire member proximal end 1102, a wire member distal end 1104, a lengthwise axis 1101 that extends from the wire member proximal end 1102 to the wire member distal end 1104, a first portion 1106 that defines a first outer diameter 1107, a first exterior surface 1114, and a first portion length 1119, a second portion 1108 that defines a second outer diameter 1109, a second exterior surface 1116, and a second portion length 1121, a flange 1110 that defines a third outer diameter 1111 and a flange surface 1112, and a tip 1118 defined at the wire member distal end 1104. The wire member 1100 is made of a first material.

In the illustrated embodiment, the first portion 1106 extends from the wire member proximal end 1102 toward the wire member distal end 1104. The second portion 1108 extends from the wire member distal end 1104 toward the wire member proximal end 1102. In the illustrated embodiment, the first portion length 1119 is greater than the second portion length 1121 and the first outer diameter 1107 is greater than the second outer diameter 1109. The flange 1110 is disposed between the wire member proximal end 1102 and the wire member distal end 1104 and extends radially outward from the wire member 1100. In the illustrated embodiment, the third outer diameter 1111 is greater than the second outer diameter 1109 and is equal to the first outer diameter 1107. The flange surface 1112 faces towards the wire member distal end 1104 and is configured to engage the retaining member 1500, which is described in more detail below. The structural interface between the flange 1110 on the wire member 1100 is considered advantageous at least because the flange 1110 can limit linear movement of the retaining member 1500 along the second portion 1108 when the retaining member 1500 directly contacts the flange 1110, which is described in more detail below.

While the illustrated embodiment describes that the flange 1110 has a third outer diameter 1111 that is greater than the second outer diameter 1109 and is equal to the first outer diameter 1107, a third outer diameter of a flange may have any suitable diameter relative to a first and second outer diameter. Selection of a suitable third outside diameter for a flange can be based on various considerations, including the size, shape, and configuration of a retaining member, the diameters of the first and second portions, and other considerations. Examples of suitable third outer diameters for a flange include a third outer diameter that is greater than the first and second outer diameters, a third outer diameter greater than the second outer diameter and equal to the first outer diameter, a third outer diameter greater than the second outer diameter and less than the first outer diameter, a third outer diameter less than the first and second outer diameters, and any other third outer diameters for a flange considered suitable for a particular embodiment.

In the illustrated embodiment, the wire member 1100 is a solid wire. It is noted, though, that a lumen-defining structure, such as a cannula, can also be used as the wire member in a temporary fixation device according to a particular embodiment.

Figure 4:
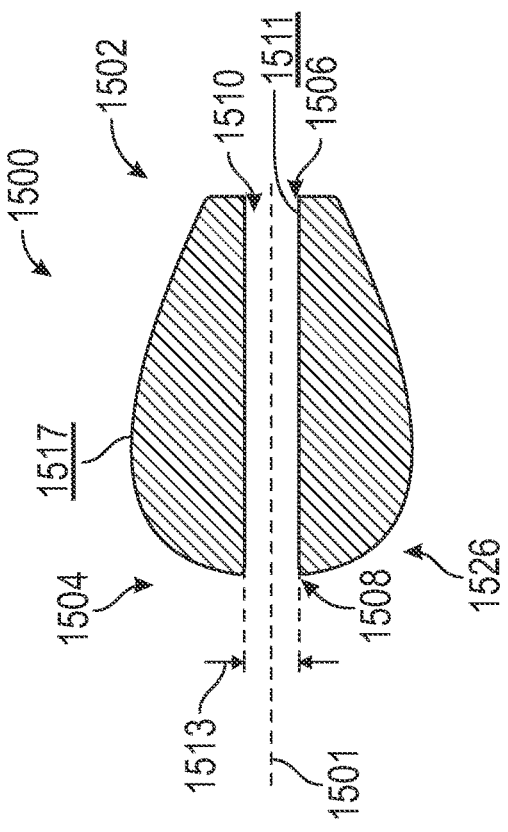
FIG. 4 is a cross-sectional view of the retaining member of the temporary fixation device illustrated in FIG. 2.
Figure 5:
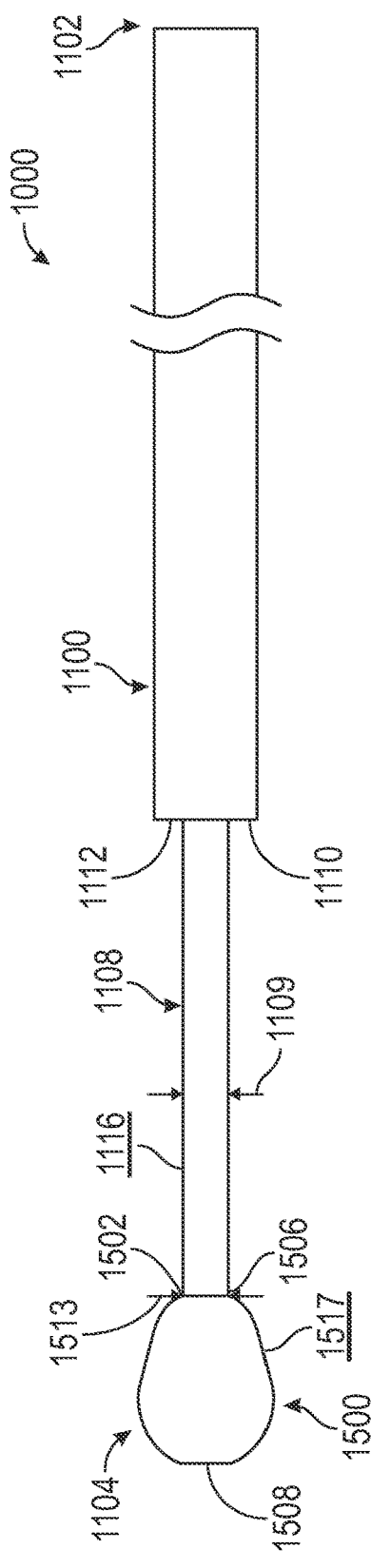
FIG. 5 is a side view of the temporary fixation device illustrated in FIG. 1. The temporary fixation device is shown in the first configuration.
Figure 6:
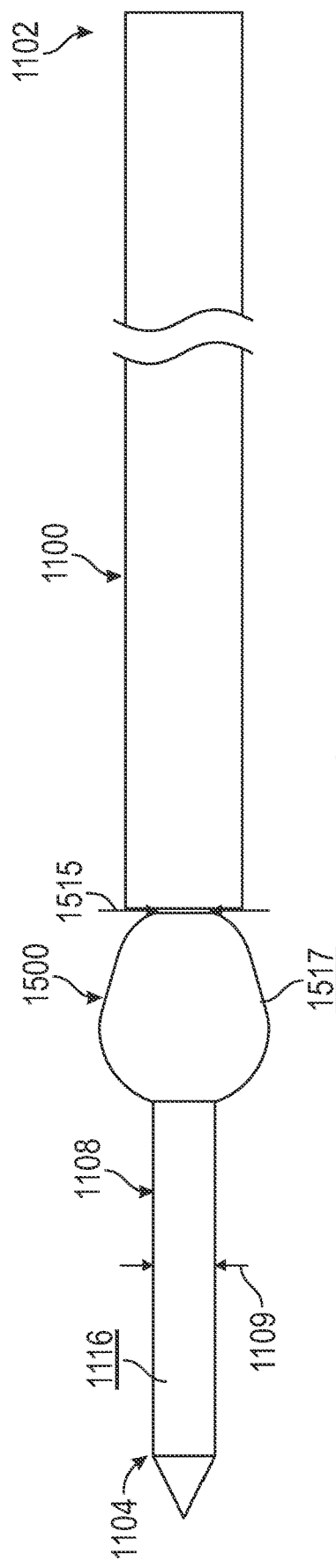
FIG. 6. is a side view of the temporary fixation device illustrated in FIG. 1. The temporary fixation device is shown in the second configuration.

As illustrated in FIG. 4, the retaining member 1500 has a retaining member proximal end 1502, a retaining member distal end 1504, a lengthwise axis 1501 that extends from the retaining member proximal end 1502 to the retaining member distal end 1504, a first opening 1506 defined at the retaining member proximal end 1502, a second opening 1508 defined at the retaining member distal end 1504, a passageway 1510, an interior surface 1511, a first inner diameter 1513, a second inner diameter 1515, an exterior surface 1517, and a distal end portion 1526. The retaining member 1500 is made of a second material. The retaining member 1500 is moveable between a first position, as shown in FIG. 5, and a second position, as shown in FIG. 6.

In the illustrated embodiment, each of the first and second openings 1506, 1508 provides access to the passageway 1510 such that the passageway 1510 has access to the exterior environment. The interior surface 1511 is disposed within the passageway 1510 and extends from the first opening 1506 to the second openings 1508. The exterior surface 1517 of the retaining member 1517 extends from the retaining member proximal end 1502 to the retaining member distal end 1504. Each of the first opening 1506, the second opening 1508, and the passageway 1510 defines the first inner diameter 1513 such that the first inner diameter 1513 is constant throughout the retaining member 1500. In the illustrated embodiment, the first inner diameter 1513 of the retaining member 1500 is less than second outer diameter 1109 of the second portion 1108 prior to engaging the second portion 1108, and the second inner diameter 1515 of the retaining member 1500 is greater than the second outer diameter 1109 of the second portion 1108 when engaging the second portion 1108.

The retaining member 1500 has a tapered-shape such that a portion of the retaining member 1500 that extends from the retaining member distal end 1504 toward the retaining member proximal end 1502 defines a greater diameter than a portion of the retaining 1500 that extends from the retaining member proximal end 1502 toward the retaining member distal end 1504. The distal end portion 1526 extends from the retaining member distal end 1504 toward the retaining member proximal end 1502 and defines a rounded-shape. The distal end portion 1526 is sized and configured to engage an opening of a bone plate during use, which is described in more detail below. The shape of the retaining member 1500 is considered advantageous at least because the shape allows the user, such as a surgeon, to manipulate the temporary fixation device 1000 at any suitable angle relative to the surface of the patient's bone and/or an opening of a bone plate when temporarily fixing the temporary fixation device 1000, which is described in more detail below.

While the distal end portion 1526 defines a rounded-shape, a distal end portion may define any suitable shape. Selection of a suitable shape for a distal end portion can be based on various consideration, including the size, shape, and configuration of the openings on a bone plate. Examples of suitable shapes for a distal end portion include round, curvilinear, arcuate, elliptical, parabolic, hyperbolic, circular, ovoid, spherical, conical, and any other suitable shapes for a particular embodiment.

The structural configuration of the retaining member 1500 and the wire member 1110 is considered advantageous at least because the second outer diameter 1109 creates a friction fit with the first inner diameter 1513 to militate against, but allow, movement of the retaining member 1500 along the second portion 1108. The second material of the retaining member 1500 is a resilient material such that the retaining member 1500 can provide a first inner diameter 1513 prior to engaging the second portion 1108 and a second inner diameter 1515 when engaging the second portion 1108. Such material of the retaining members allows attachment and movement of the retaining member 1500 along the second portion 1108. Furthermore, the shape of the retaining member 1500 is considered advantageous at least because the distal end portion 1526 is sized and configured to interact with and directly contact a bone plate, such as bone plate 4800 illustrated in FIG. 30 and described below, for utilizing a structural interface that centers the temporary fixation device 1000 with an opening of the set of openings 4806 on a bone plate 4800, which is described in more detail below. Such shape of the retaining member 1500 allows the retaining member 1500 to engage the entire opening on a bone plate during the temporary attachment of a bone plate to a patient's bone, which is described in more detail below.

While the retaining member 1500 and wire member 1100 are configured to create a friction fit due to the retaining member 1500 defining the first inner diameter 1513 prior to engaging the second portion 1108 and defining the second inner diameter 1515 when engaged with the second portion 1108, a retaining member can have any suitable first and second inner diameters to create a friction fit with a wire member. Selection of suitable first and second inner diameter for a retaining member can be based on various considerations, including the type of materials used to manufacture a wire member with a first material and a retaining member with a second material.

FIG. 5 illustrates the temporary fixation device 1000 in a first configuration, and FIG. 6 illustrates the temporary fixation device 1000 in a second configuration.

When the temporary fixation device 1000 is in the first configuration, the retaining member 1500 is in the first position. In the first position, the retaining member 1500 is positioned along a portion of the second portion 1108 that is closer to the wire member distal end 1104. The tip 1118 and a portion of the second portion 1108 pass through the first opening 1506 and are disposed within the passageway 1510. The interior surface 1511 of the retaining member 1500 and the second exterior surface 1116 of the second portion 1108 are in direct contact with each other along a portion of the passageway 1510 measured from the first opening 1506 to a location between the first opening 1506 and the second opening 1508 and along a portion of the second portion 1108 closer to the wire member distal end 1504. In the first position, the first opening 1506 and a portion of the passageway 1510 measured from the first opening 1506 to a location between the first opening 1506 and the second opening 1508 defines the second inner diameter 1515. In the first position, the second opening 1508 and a portion of the passageway 1510 measured from the second opening 1508 to a location between the first opening 1506 to the second opening 1508 defines the first inner diameter 1513. The second inner diameter 1515 is greater than the first inner diameter 1513 and the second outer diameter 1109.

When the temporary fixation device 1000 is in the second configuration, the retaining member 1500 is in the second position. In the second position, the retaining member 1500 is disposed at a location between the wire member proximal end 1102 and the wire member distal end 1104 along the second portion 1108 closer to the flange 1110. The retaining member 1500 is directly contacting the flange 1110 such that the exterior surface 1517 of the retaining member 1500 at the retaining member proximal end 1502 and the flange surface 1112 are in direct contact with each other. The flange 1110 prevents linear movement of the retaining member 1500 along the second portion 1108. The interior surface 1511 of the retaining member 1500 and the second exterior surface 1116 of the second portion 1108 are in direct contact with each other along the entire retaining member 1500 and a portion of the second portion 1108. Each of the first opening 1506, the second opening 1508, and the passageway 1510 defines the second inner diameter 1515 when the retaining member 1500 reaches its second position.

In use, an external force is exerted against the temporary fixation device 1000 such that the external force is exerted against the wire member 1100 at the wire member proximal end 1102. The force is accomplished by exerting the force on the first exterior surface 1114 in which the force is directed toward the wire member distal end 1104. As the tip 1118 and retaining member 1500 engage a patient's bone due to the force exerted on the wire member 1100, the retaining member 1500 moves linearly along the second portion 1108 toward the wire member proximal end 1102 opposite to the direction of the external force exerted on the wire member 1100. During the movement of the retaining member 1500 from its first position to its second position, each of the first opening 1506, the second opening 1508, and the passageway 1510 defines the second inner diameter 1515. The transition between the first inner diameter 1513 to the second inner diameter 1515 allows the retaining member 1500 to constantly engage the second portion 1108 during movement such that the wire member 1100 and retaining member 1500 are frictionally fit to each other. The temporary fixation device 1000 has met its desired depth within the patient's bone once the exterior surface 1517 of the retaining member 1500 at the retaining member proximal end 1502 directly contacts the flange surface 1112 such that the flange 1110 prevents linear movement of the retaining member 1500. Once the exerted force ceases, the retaining member 1500 maintains its position on the second portion 1108.

Figure 7:
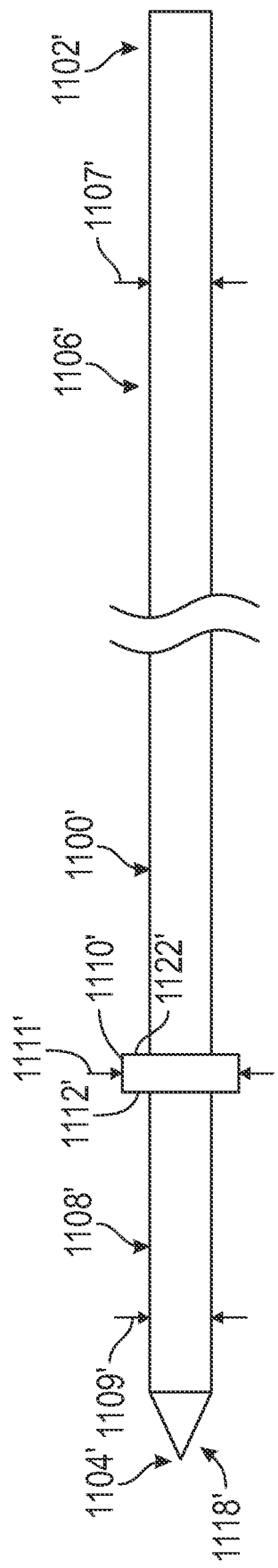
FIG. 7 is a side view of another example temporary fixation device.

FIG. 7 illustrates an alternative wire member 1100'. The wire member 1100' has a wire member proximal end 1102', a wire member distal end 1104', a first portion 1106' that defines a first outer diameter 1107', a second portion 1108' that defines a second outer diameter 1109', and a flange 1110' that defines a third outer diameter 1111', a flange first surface 1112', and a flange second surface 1122'. In the illustrated embodiment, the third outer diameter 1111' is greater than the first and second outer diameters 1107', 1109'. The flange first surface 1112' is disposed closer to the wire member distal end 1104' and faces the wire member distal end 1104'. The flange second surface 1122' is disposed closer to the wire member proximal end 1102' and faces the wire member proximal end 1102'. The flange first and second surfaces 1112', 1122' are parallel to each other, but directly oppose each other.

Figure 8:
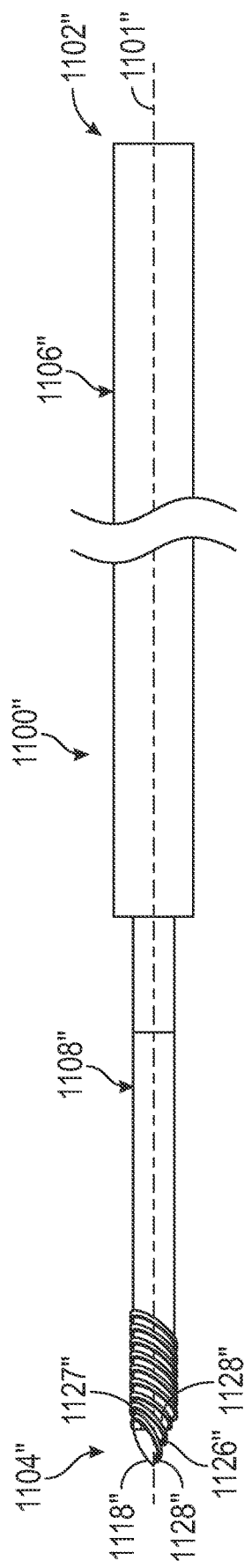
FIG. 8 is a side view of another example temporary fixation device.
Figure 9:
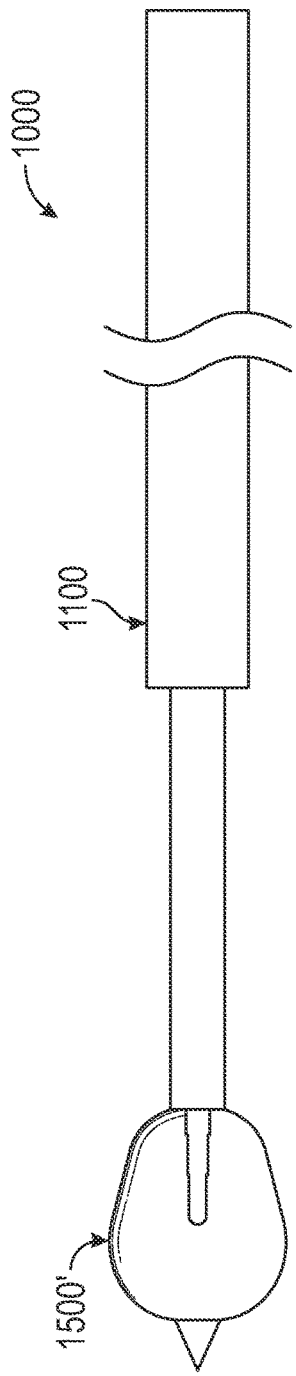
FIG. 9 is a side view of another example temporary fixation device.
Figure 10:
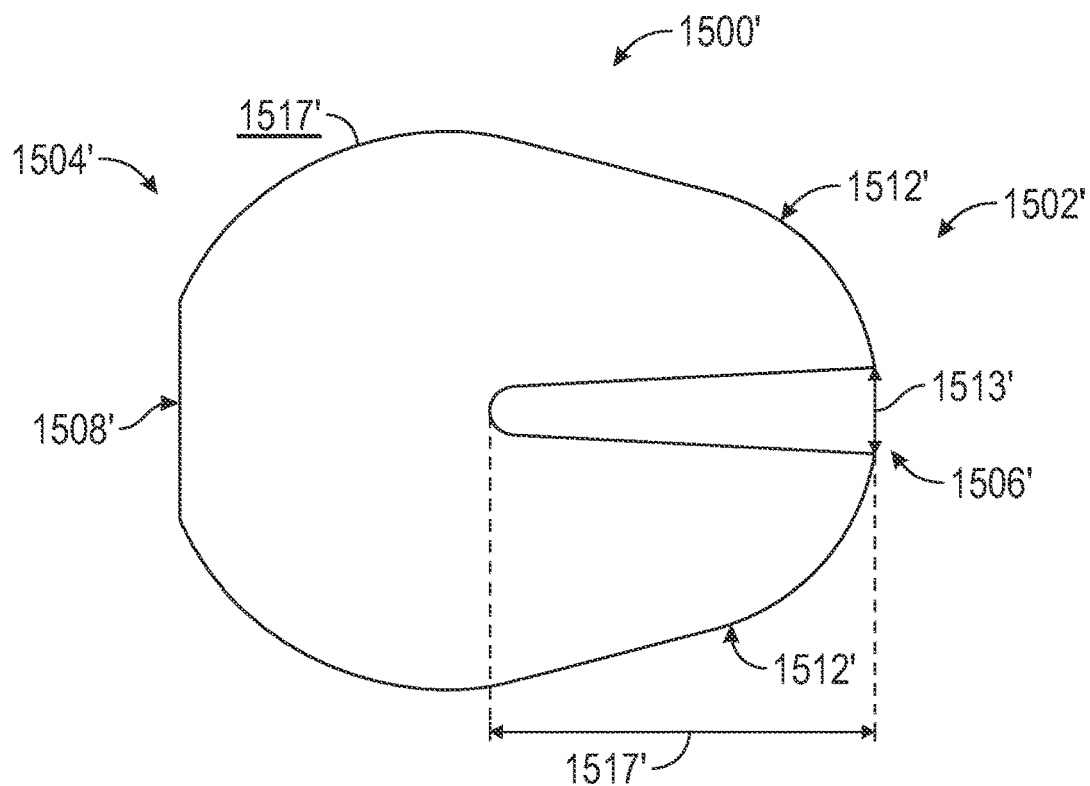
FIG. 10 is a side view of the retaining member of the temporary fixation device illustrated in FIG. 9.

FIG. 8 illustrates an alternative wire member 1100". The wire member 1100" defines at least one cutting flute 1126" and at least one cutting edge 1128". In the illustrated embodiment, each cutting flute 1126" and each cutting edge 1128" extends along the tip 1118" and along a portion of the second portion 1108" from the wire member distal end 1104" to a location between the wire member proximal end 1102" and the wire member distal end 1104". Each cutting flute 1126" extends into the wire member 1100" along an axis that is perpendicular to the lengthwise axis 1101" of the wire member 1100" at a depth 1127". Each cutting flute 1126" and each cutting edge 1128" is disposed circumferentially about the second portion 1108" such that each cutting flute 1126" and each cutting edge 1128" is helically disposed about the tip 1118' and a portion of the second portion 1108". Each cutting edge 1128" is also continuous and uninterrupted along the tip 1118' and a portion of the second portion 1108".

While the wire member 1100" defines at least one cutting flute 1126" and at least one cutting edge 1128" on the second portion 1108", a wire member can have any suitable number of cutting flutes and cutting edges disposed on a second portion. Selection of a suitable number of cutting flutes and cutting edges can be based on various considerations, including the amount of material to be removed from a patient's bone, the amount of time to position a temporary fixation device in a patient's bone, and other considerations. Examples of suitable numbers of cutting flutes and cutting edges disposed on a second portion include one, at least one, plurality, two, three, four, five, six, and any other suitable numbers of cutting flutes and cutting edges disposed on a second portion—for a particular embodiment.

Figure 11:
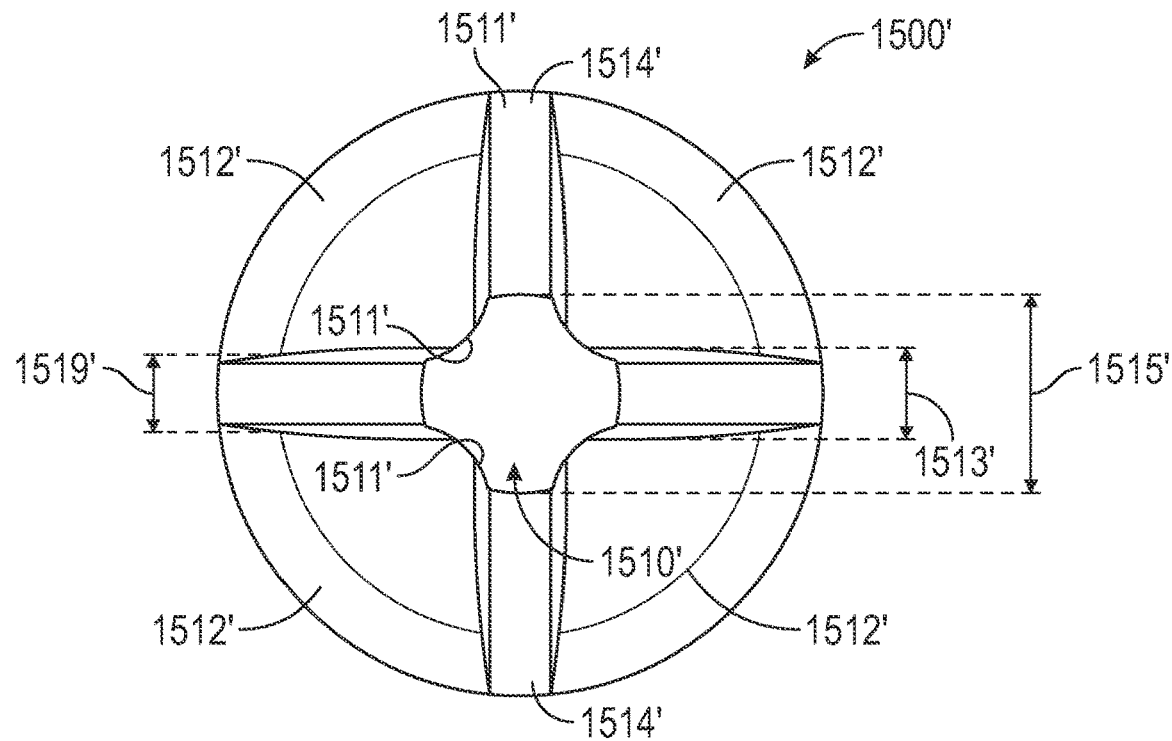
FIG. 11 is a front view of the retaining member of the temporary fixation device illustrated in FIG. 9.
Figure 12:
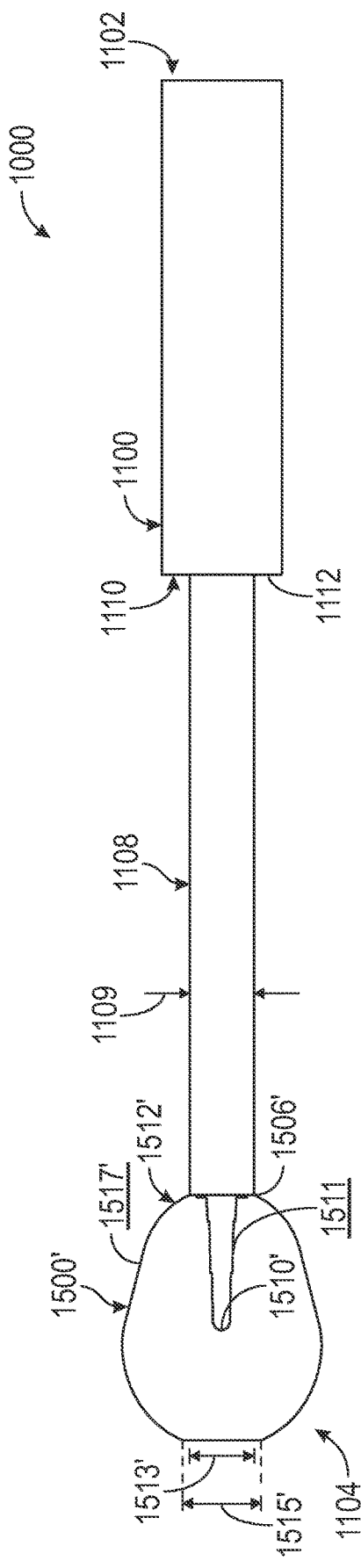
FIG. 12 is a partial side view of the temporary fixation device illustrated in FIG. 9. The temporary fixation device is shown in the first configuration.
Figure 13:
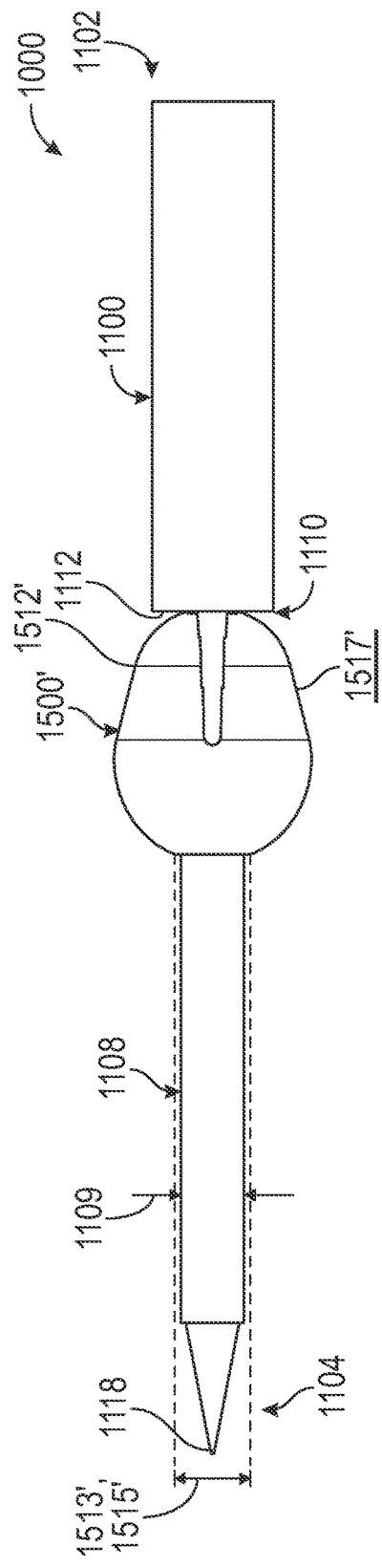
FIG. 13 is a partial side view of the temporary fixation device illustrated in FIG. 9. The temporary fixation device is shown in the second configuration.
Figure 14:
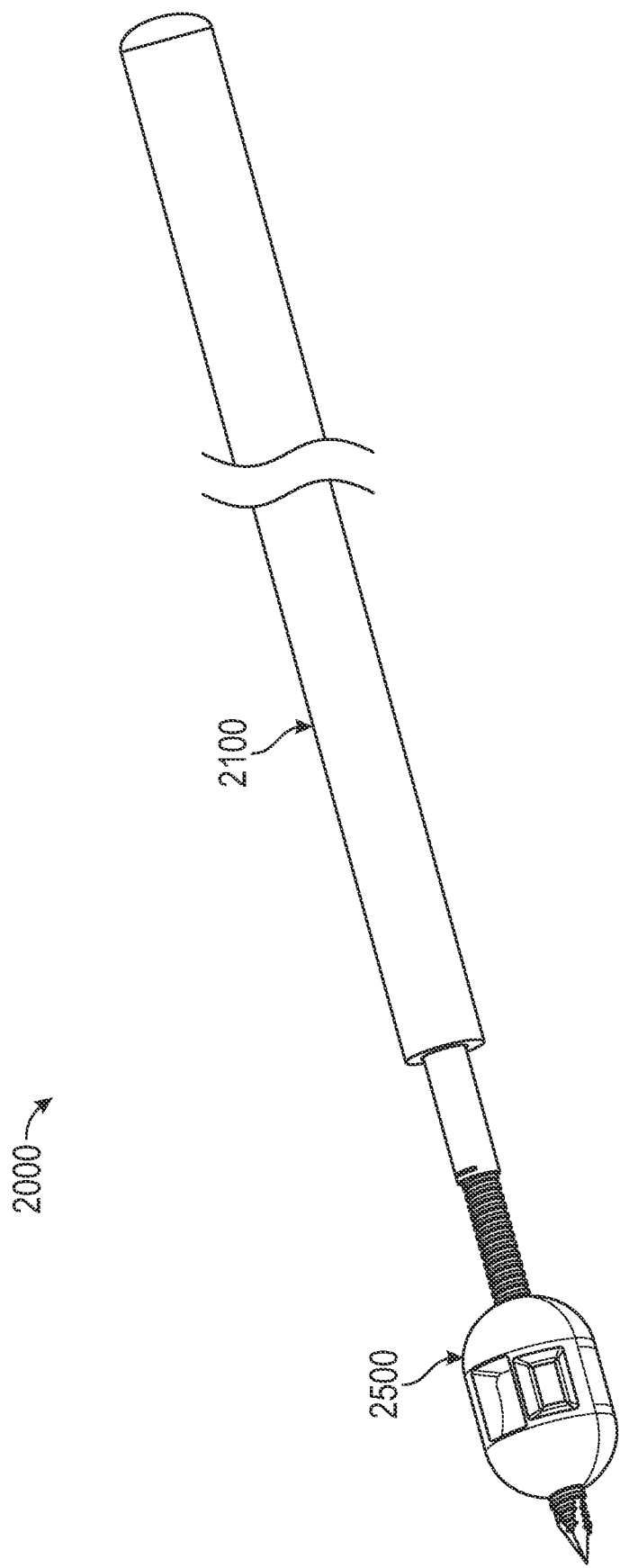
FIG. 14 is a perspective view of another example temporary fixation device.
Figure 15:
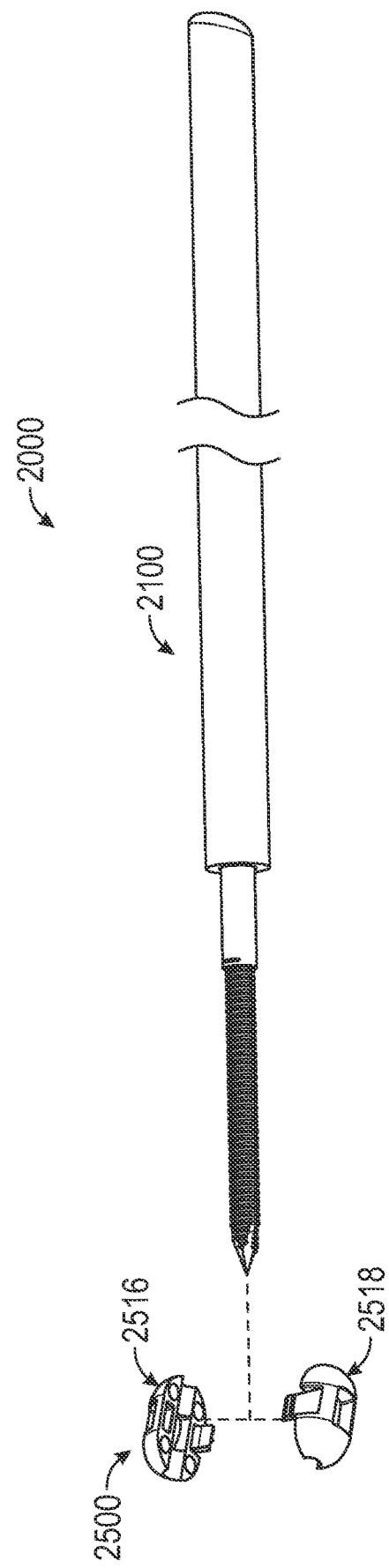
FIG. 15 is an exploded view of the example temporary fixation device illustrated in FIG. 14.

FIGS. 9 through 13 illustrate an alternative retaining member 1500' that includes a set of extensions 1512' and a set of channels 1514'. The retaining member is moveable between a first position, as shown in FIG. 12, and a second position, as shown in FIG. 13.

In the illustrated embodiment, each extension of the set of extensions 1512' extends along a portion of the retaining member 1500' from the retaining member proximal end 1502' to a location between the retaining member proximal end 1502' and the retaining member distal end 1504'. Each extension of the set of extensions 1512' is independent of each other such that each extension 1512' moves independently during use, which is described in more detail below. Each extension of the set of extensions 1512' is separated by a channel from the set of channels 1514'. Each channel of the set of channels 1514' extends along an axis that this parallel to the lengthwise axis 1501' of the retaining member 1500' and defines a channel length 1517' and a channel width 1519'. Each channel of the set of channels 1514' provides a space between each extension of the set of extensions 1512' such that each extension of the set of extensions 1512' can extend away from retaining member 1500' once the set of extensions engages a wire member (e.g. wire member 1000).

While the retaining member 1500' illustrates a set of extensions 1512' and a set of channels 1514', a retaining member can have any suitable number of extensions and channels. Selection of a suitable number of extensions and channels can be based various considerations, including the size, shape, and configuration of a retaining member and a wire member, the type of materials used for a retaining member and a wire member, and other considerations. Examples of suitable numbers of extensions and channels on a retaining member include one, at least one, two, plurality, three, four, five, six, and any other numbers of extensions and channels on a retaining member considered suitable for a particular embodiment. As illustrated in FIG. 11, the retaining member 1500' includes four extensions for the set of extensions 1512' and four channels for the set of channels 1514'.

The set of extensions 1512' defines the first opening 1506' of the retaining member 1500' at the retaining member proximal end 1502'. However, in this embodiment, the passageway 1510' does not extend along the entire retaining member 1500'. Rather, the passageway 1510' only extends along a portion of the retaining member 1500' between the second opening 1508' and the set of extensions 1512'. The passageway 1510' terminates at the location where the set of extensions 1512' is positioned on the retaining member 1500'.

The set of extensions 1512' is considered advantageous at least because the set of extensions 1512' provides an additional friction fit between the retaining member 1500' and the second portion 1108 when the retaining member 1500' transitions from its first position to its second position along the second portion 1108. The set of extensions 1512' allows a user, such as a surgeon, to manipulate the wire member 1110 at any suitable angles when the temporary fixation device 1000 is engaging either a patient's bone or a bone plate, which is described in more detail below. During manipulation of the wire member 1100, at least one extension of the set of extensions 1512' engages the second portion 1108 in order to provide a friction fit between the retaining member 1500 and the wire member 1100. Furthermore, the set of extensions 1512' allows for relaxed tolerances between the second portion 1108 and the retaining member 1500', specifically the tolerances between the second outer diameter 1108 and the first and second inner diameters 1513', 1515'. The set of extensions 1512' provides easier manufacturing techniques and solutions for producing each of the retaining member 1500' and the wire member 1100.

FIG. 12 illustrates the temporary fixation device 1000 in a first configuration, and FIG. 13 illustrates the temporary fixation device 1000 in a second configuration.

When the temporary fixation device 1000 is in the first configuration, the retaining member 1500' is in the first position. In the first position, the retaining member 1500' is positioned along a portion of the second portion 1108 that is closer to the wire member distal end 1104. The tip 1118 and a portion of the second portion 1108 pass through the first opening 1506' and are disposed between the set of extensions 1512' and within the passageway 1510'. The interior surface 1511' of the retaining member 1500' and the second exterior surface 1116 of the second portion 1108 are in direct contact with each other along the set of extensions 1512' and along a portion of the second portion 1108 closer to the wire member distal end 1104. In the first position, the retaining member 1500' defines the second inner diameter 1515' at the first opening 1506' and along the set of extensions 1512' and defines the second inner diameter 1515' along each of the second opening 1508' and the passageway 1510'. The set of extensions 1512' extends away from the lengthwise axis 1501' of the retaining member 1500' and engages the wire member second portion 1108 in which the first inner diameter 1513' and the second inner diameter 1515' are substantially equal and each of first and second inner diameters 1513', 1515' is greater than the second outer diameter 1109.

When the temporary fixation device 1000 is in the second configuration, the retaining member 1500' is in the second position. In the second position, retaining member 1500' is disposed at a location between the wire member proximal end 1102 and the wire member distal end 1104 along the second portion 1108 closer to the flange 1110. The set of extensions 1512' continue to extend away from the lengthwise axis 1501' of the retaining member 1500' when engaging the wire member second portion 1108 and transitioning from the first position to the second position. In the second position, the set of extensions 1512' engages the flange surface 1112 to prevent linear movement of the retaining member 1500' and to maintain the retaining member 1500' at the second position. The flange 1110 prevents linear movement of the retaining member 1500' along the second portion 1108.

In use, an external force is exerted against the temporary fixation device 1000 such that the external force is exerted against the wire member 1100 at the wire member proximal end 1102. The force is accomplished by exerting the force on the first exterior surface 1114 in which the force is directed toward the wire member distal end 1104. As the tip 1118 and retaining member 1500' engage a patient's bone due to the force exerted on the wire member 1100, the retaining member 1500 moves linearly along the second portion 1108 toward the wire member proximal end 1102 opposite to the direction of the external force exerted on the wire member 1100. During the movement of the retaining member 1500 from its first position to its second position, each extension of the set of extensions 1512' extends away from the wire member second portion 1108 once the retaining member 1500' engages the wire member 1100. During the movement of the retaining member 1500' from its first position to its second position, the first inner diameter 1513' and the second inner diameter 1515' become substantially equally to each other. The transition between the first inner diameter 1513' to the second inner diameter 1515' allows the retaining member 1500' to constantly engage the second portion 1108 during movement such that the wire member 1100 and retaining member 1500' are frictionally fit to each other. At least one extension of the set of extensions 1512' directly contacts and engages the second portion 1108 during its transition from the first position to the second position. The temporary fixation device 1000 has met its desired depth within the patient's bone once the exterior surface 1517' of the retaining member 1500' at the retaining member proximal end 1502' directly contacts the flange surface 1112 such that the flange 1110 prevents further linear movement of the retaining member 1500'. Once the exerted force ceases, the retaining member 1500' maintains its position on the second portion 1108.

The wire member in a temporary fixation device according to an embodiment can be made from any material suitable for use in medical devices intended for orthopedic use, including materials suitable for use in procedural tools and materials suitable for use in long-term implants. Examples of suitable materials for use in wire members in temporary fixation devices according to embodiments include metals, metal alloys, and polymeric materials, including plastics. Examples of suitable metals include, but are not limited to, Titanium, Magnesium, and other metals. Examples of suitable metal alloys include, but are not limited to, stainless steel, Ti6Al4V, 316 LVM, 1.4441Ti-13Nb-13Zr, Ti-12Mo-6Zr-2Fe, Ti-15Mo-5Zr-3Al, Ti15Mo, Ti-35Nb-7Zr-5Ta and Ti-29Nb-13Ta-4.6Zr Ti-6Al-7Nb and Ti-15Sn-4Nb-2Ta-0.2Pd Co—Cr—Mo alloys. Examples of suitable polymeric materials include, but are not limited to, polyaryletherketone (PAEK), polyether ether ketone (PEEK), PEEK (90G, 450G, I2, I4), Polyamid, PA66, carbon fiber reinforced polyaryletherketone (CFR PAEK), polyether ketone ketone (PEKK), carbon fiber reinforced polyether ketone ketone (CFR PEKK), carbon fiber reinforced polyether ether ketone (CFR PEEK), CFR PEEK (90G CA30, 90G CA20, 450G CA30, 450G CA20, I2 CF20, I2 CF30, I4 CF30, I4 CF20), Polyamid CFR, and PA66 CFR.

The retaining member in a temporary fixation device according to an embodiment can be made from any material suitable for use in medical devices intended for orthopedic use, including materials suitable for use in procedural tools and materials suitable for use in long-term implants. Examples of suitable materials for use in retaining members in temporary fixation devices according to embodiments include resilient materials, such as elastomers, rubbers, silicone, Neoprene, plastics, and other suitable materials.

FIGS. 14 through 22 illustrate another temporary fixation device 2000. The temporary fixation device 2000 is similar to the temporary fixation device 1000 illustrated in FIGS. 1 through 6 and described above, except as detailed below. The temporary fixation device 2000 includes a wire member 2100 and a retaining member 2500.

Figure 16:
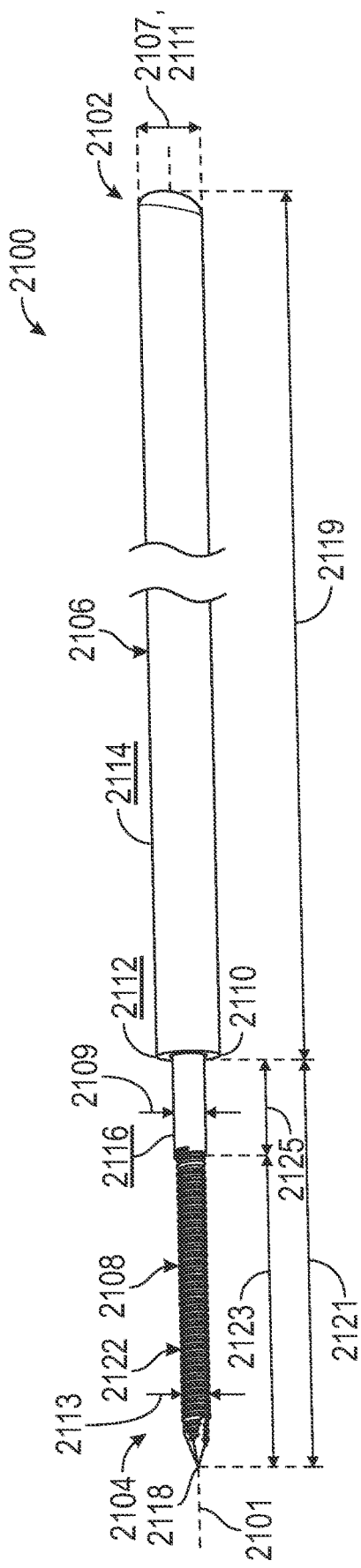
FIG. 16 is a side view of the wire member of the temporary fixation device illustrated in FIG. 14.

As illustrated in FIG. 16, the wire member 2100 has a wire member proximal end 2102, a wire member distal end 2104, a lengthwise axis 2101 that extends from the wire member proximal end 2102 to the wire member distal end 2104, a wire member first portion 2106 that defines a first outer diameter 2107, a first exterior surface 2114, and a first portion length 2119, a wire member second portion 2108 that defines a second outer diameter 2109, a second exterior surface 2116, and a second portion length 2121, a flange 2110 that defines a third outer diameter 2111 and a flange surface 2112, a tip 2118 defined at the wire member distal end 2104, and a set of ridges 2122 that defines a fourth outer diameter 2113, and a length 2123. The wire member 2100 is made of a first material similar to the wire member 1100 of the temporary fixation device 1000 described above.

In the illustrated embodiment, the wire member first portion 2106 extends from the wire member proximal end 2102 toward the wire member distal end 2104. The wire member second portion 2108 extends from the wire member distal end 2104 toward the wire member proximal end 2102. In the illustrated embodiment, the first portion length 2119 is greater than the second portion length 2121 and the first outer diameter 2107 is greater than the second outer diameter 2109. The flange 2110 is disposed between the wire member proximal end 2102 and the wire member distal end 2104 and extends radially outward from the wire member 2100. In the illustrated embodiment, the third outer diameter 2111 is greater than the second outer diameter 2109 and is equal to the first outer diameter 2107. The flange surface 2112 faces towards the wire member distal end 2104 and can be configured to engage the retaining member 2500, which is described in more detail below. The structural interface between the flange 2110 on the wire member 2100 is considered advantageous at least because the flange 2110 can limit linear movement of the retaining member 2500 along the wire member second portion 2108 when the retaining member 2500 directly contacts the flange 2110, which is described in more detail below.

As illustrated in FIG. 16, the set of ridges 2122 is disposed along a portion of the wire member second portion 2108 that extends from the wire member distal end 2104 to a location between the wire member proximal end 2102 and the wire member distal end 2104 to define the length 2123. A portion of the second exterior surface 2116 between the set of ridges 2122 and the flange 2110 is continuous and uninterrupted from the set of ridges 2122 and defines a length 2125. In the illustrated embodiment, the length 2123 of the set of ridges 2122 is less than the second portion length 2121 and is greater than the length 2125 of the second exterior surface 2116 that is continuous and uninterrupted by the set of ridges 2122. Alternatively, the length 2123 of set of ridges 2122 can be equal to the second portion length 2121 such that the second exterior surface 2116 is completely interrupted by the set of ridges 2122. Alternatively, the length 2123 of the set of ridges 2122 can be less than the length 2125 of the second exterior surface 2116 that is continuous and uninterrupted by the set of ridges 2122. Each ridge of the set of ridges 2122 extends radially outward from the second exterior surface 2116 along an axis that is perpendicular to the lengthwise axis 2101 of the wire member 2100 to define the fourth outer diameter 2113. In the illustrated embodiment, the fourth outer diameter 2113 is greater than the second outer diameter 2109 and less than the first and third outer diameters 2107, 2111. Alternatively, the fourth outer diameter 2113 can be greater than the first outer diameter 2107 and/or greater than the third outer diameter 2111.

The set of ridges 2122 that is disposed along a portion of the wire member second portion 2108 is considered advantageous at least because the set of ridges 2122 interacts with and directly contacts each of the first and second arms 2534, 2554 of the retaining member 2500 such that the retaining member 2500 attaches to and moves along wire member second portion 2108 during use, which is described in more detail below. The interaction between the set of ridges 2122 and the retaining member 2500 provides a mechanical mechanism in which each ridge of the set of ridges 2122 is sized and configured to allow each of the first and second arms 2534, 2554 of the retaining member 2500 to be disposed between each ridge of the set of ridges 2122. The mechanical mechanism between the set of ridges 2122 and the first and second arms 2534, 2554 allows the retaining member 2500 to incrementally move along the wire member second portion 2108, which is similar to that of a ratcheting mechanism. Furthermore, such interaction between the set of ridges 2122 and the first and second arms 2534, 2554 of the retaining member 2500 allows the retaining member 2500 to maintain a desired position along the wire member second portion 2108.

While the wire member 2100 includes a certain structural configuration (e.g., set of ridges 2122) along a portion of the wire member second portion 2108, a wire member can include any suitable structural configuration along a portion of a wire member second portion. Selection of a suitable structural configuration along a wire member second portion can be based various considerations, including the size, shape, and configuration of a retaining member, the type of materials used for a retaining member and a wire member, the amount of force exerted on a retaining member and a wire member, and other considerations. Examples of suitable structural configurations disposed along a wire member second portion include a set of grooves helically disposed about a wire member second portion, a set of recesses extending into a wire member second portion, a set of depressions extending into a wire member second portion, a set of ribs extending away from a wire member second portion, a set of protuberances extending away from a wire member second portion, and any other structural configurations suitable for a particular embodiment.

As illustrated in FIGS. 17 through 20, the retaining member 2500 has a retaining member proximal end 2502, a retaining member distal end 2504, a lengthwise axis 2501 that extends from the retaining member proximal end 2502 to the retaining member distal end 2504, a first opening 2506 defined at the retaining member proximal end 2502, a second opening 2508 defined at the retaining member distal end 2504, a first passageway 2510, an interior surface 2511, a first inner diameter 2513, a retaining member first portion 2516, a retaining member second portion 2518, and a distal end portion 2560 that extends from the retaining member distal end 2504 toward the retaining member proximal end 2502 and defines a rounded-shape. The retaining member first portion 2516 includes a first attachment member 2520, a first receiving member 2522, a first protuberance 2524, a second protuberance 2526, a first cavity 2528, a second cavity 2530, a second passageway 2532, and a first arm 2534. The retaining member second portion 2518 includes a second attachment member 2540, a second receiving member 2542, a third protuberance 2544, a fourth protuberance 2546, a third cavity 2548, a fourth cavity 2550, a third passageway 2552, and a second arm 2554. The retaining member 2500 is made of a second material. The retaining member 2500 is moveable between a first position, as shown in FIG. 21, and a second position, as shown in FIG. 22.

In the illustrated embodiment, the retaining member 2500 is separable such that the retaining member first portion 2516 and the retaining member second portion 2518 attach to each other to form the retaining member 2500. The retaining member first portion 2516 and the retaining member second portion 2518 cooperatively define the first opening 2506, the second opening 2508, the first passageway 2510, the interior surface 2511, and the first inner diameter 2513 when the retaining member first portion 2516 and the retaining second portion 2518 are attached to each other. Alternatively, the retaining member 2500 can be unitary such that the retaining member first portion 2516 and the retaining member second portion 2518 are a single, unitary member.

The first attachment member 2520 is disposed between the retaining member proximal and distal ends 2502, 2504 on the retaining member first portion 2516 and extends away from the retaining member first portion 2516 along an axis that is perpendicular to the lengthwise axis 2501 and the first passageway 2510. The first receiving member 2522 is disposed between the retaining member proximal and distal ends 2502, 2504 on the retaining member first portion 2516 and extends into the retaining member first portion 2516 along an axis that is perpendicular to the lengthwise axis 2501 and the first passageway 2510. In the illustrated embodiment, the first receiving member 2522 is sized and configured to receive and secure the second attachment member 2540 such that the first receiving member 2522 and the second attachment member 2540 are attached by a snap-fit mechanism. The first attachment member 2520 and the first receiving member 2522 are parallel to each other on the retaining member first portion 2516, but directly oppose each other. The second attachment member 2540 is disposed between the retaining member proximal and distal ends 2502, 2504 on the retaining member second portion 2518 and extends away from the retaining member second portion 2518 along an axis that is perpendicular to the lengthwise axis 2501 and the first passageway 2510. The second receiving member 2542 is disposed between the retaining member proximal and distal ends 2502, 2504 on the retaining member second portion 2518 and extends into the retaining member second portion 2518 along an axis that is perpendicular to the lengthwise axis 2501 and the first passageway 2510. The second receiving member 2542 is sized and configured to receive and secure the first attachment member 2520 such that the second receiving member 2542 and the first attachment member 2520 are attached by a snap-fit mechanism. The second attachment member 2540 and the second receiving member 2542 are parallel to each other on the retaining member second portion 2518, but directly oppose each other.

The first protuberance 2524 is disposed between the retaining member distal end 2504 and the first receiving member 2522 and extends from the retaining member first portion 2516 along an axis that is perpendicular to the lengthwise axis 2501. The second protuberance 2526 is disposed between the retaining member proximal end 2502 and the first receiving member 2522 and extends from the retaining member first portion 2516 along an axis that is perpendicular to the lengthwise axis 2501. The first cavity 2528 is disposed between the retaining member distal end 2504 and the first attachment member 2520 and extends into the retaining member first portion 2516 along axis that is perpendicular to the lengthwise axis 2501. The first cavity 2528 is sized and configured to receive and house the third protuberance 2544. The second cavity 2530 is disposed between the retaining member proximal end 2502 and the first attachment member 2520 and extends into the retaining member first portion 2516 along axis that is perpendicular to the lengthwise axis 2501. The second cavity 2530 is sized and configured to receive and house the fourth protuberance 2546. The third protuberance 2544 is disposed between the retaining member distal end 2504 and the second receiving member 2542 and extends from the retaining member second portion 2518 along an axis that is perpendicular to the lengthwise axis 2501. The fourth protuberance 2546 is disposed between the retaining member proximal end 2502 and the second receiving member 2542 and extends from the retaining member second portion 2518 along an axis that is perpendicular to the lengthwise axis 2501. The third cavity 2548 is disposed between the retaining member distal end 2504 and the second attachment member 2540 and extends into the retaining member second portion 2518 along axis that is perpendicular to the lengthwise axis 2501. The third cavity 2548 is sized and configured to receive and house the first protuberance 2524. The fourth cavity 2550 is disposed between the retaining member proximal end 2502 and the second attachment member 2540 and extends into the retaining member second portion 2518 along axis that is perpendicular to the lengthwise axis 2501. The fourth cavity 2550 is sized and configured to receive and house the second protuberance 2526.

The second passageway 2532 is disposed between the first attachment member 2520 and the first receiving member 2522. The second passageway 2532 extends entirely through retaining member first portion 2516 along an axis that is perpendicular to the lengthwise axis 2501 and the first passageway 2510. The second passageway 2532 extends from the exterior environment of the retaining member 2500 to the first passageway 2510 such that the second passageway 2532 is in communication with the first passageway 2510. The second passageway 2532 is sized and configured to allow the first arm 2534 to move inside the second passageway 2532 along an axis that is parallel to the second passageway 2532 during use, which is described in more detail below. The third passageway 2552 is disposed between the second attachment member 2540 and the second receiving member 2542. The third passageway 2552 extends entirely through the retaining member second portion 2518 along an axis that is perpendicular to the lengthwise axis 2501 and the first passageway 2510. The third passageway 2552 extends from the exterior environment of the retaining member 2500 to the first passageway 2510 such that the third passageway 2552 is in communication with the first passageway 2510. The third passageway 2552 is sized and configured to allow the second arm 2554 to move inside the third passageway 2552 along an axis that is parallel to the third passageway 2552 during use, which is described in more detail below. Once the retaining member first portion 2516 and the retaining member second portion 2518 are attached to each other, the second and third passageways 2532, 2552 are parallel to each other, but directly oppose, and each of the first passageway 2510, the second passageway 2532, and the third passageway 2552 are in communication with each other.

The first arm 2534 extends from the retaining member first portion 2516 and into the second passageway 2532. The second arm 2554 extends from the retaining member second portion 2518 and into the third passageway 2552. As illustrated in FIGS. 20 and 21, each of the first and second arms 2534, 2554 is disposed in a first position prior to the retaining member first and second portions 2516, 2518 being attached together and prior to engaging the set of ridges 2122, which is described in more detail below. Once the retaining member first and second portions 2516, 2518 are attached to each other, the first and second arms 2534, 2554 are parallel to each other relative to the lengthwise axis 2501, but oppose each other. Once the retaining member first and second portions 2516, 2518 are attached to each other, the first arm 2534 is disposed within the first and second passageways 2510, 2532 and the second arm 2554 is disposed within the first and third passageways 2510, 2552. Each of the first and second arms 2534, 2554 is sized and configured to engage the set of ridges 2122 once the retaining member 2500 engages the wire member second portion 2108, which is described in more detail below.

FIG. 21 illustrates the temporary fixation device 2000 in a first configuration, and FIG. 22 illustrates the temporary fixation device 2000 in a second configuration.

When the temporary fixation device 2000 is in the first configuration, the retaining member 2500 is in the first position. In the first position, the retaining member 2500 is positioned along a portion of the second portion 2108 closer to the wire member distal end 2104. The tip 2118 and a portion of the wire member second portion 2108 pass through the first opening 2506 and are disposed within the first passageway 2510. The interior surface 2511 of the retaining member 2500 and the set of ridges 2122 are in direct contact with each other at the retaining member first opening 2506 and along a portion of the wire member second portion 2108 closer to the wire member distal end 2104. Each of the first and second arms 2534, 2554 is disposed in the first position prior to engaging the set of ridges 2122. The first arm 2534 is disposed in the first and second passageways 2510, 2532 and is not engaged with the set of ridges 2122. The second arm 2554 is disposed in the first and third passageways 2510, 2552 and is not engaged with the set of ridges 2122. In the first position, the first and second arms 2534, 2554 cooperatively define a first distance 2561 that measures the distance between the first and second arms 2534, 2554.

When the temporary fixation device 2000 is in the second configuration, the retaining member 2500 is in the second position. In the second position, the retaining member 2500 is disposed at a location between the wire member proximal end 2102 and the wire member distal end 2104 along the wire member second portion 2108 closer to the flange 2210. A portion of the interior surface 2511 between the retaining member proximal end 2502 and the second and third passageways 2532, 2552 is in direct contact with the second exterior surface 2116. A portion of the interior surface 2511 between the retaining member distal end 2504 and the second and third passageways 2532, 2552 is in direct contact with the set of ridges 2122. Each of the first and second arms 2534, 2554 is disposed in the second position and engages the set of ridges 2122. The first arm 2534 interacts with and directly contacts a ridge of the set of ridges 2122 that is parallel to, but directly opposite to, another ridge of the set of ridges 2122 that the second arm 2554 is interacting with and directly contacting in the second position. In the second position, the first and second arms 2534, 2554 cooperatively define a second distance 2563 that measures the distance between the first and second arms 2534, 2554. The second distance 2563 between the first and second arms 2534, 2554 is greater than the first distance 2561 between the first and second arms 2534, 2554. During the transition between each ridge of the set of ridges 2122 in which each of the first and second arms 2534, 2554 engages the edge of a ridge of the set of ridges 2122, the first and second arms 2534, 2554 cooperatively define a third distance (not illustrated) that measures the distance between the first and second arms 2534, 2554. The third distance between the first and second arms 2534, 2554 is greater than the first distance 2561 measured between the first and second arms 2534, 2554 and the second distance 2563 measured between the first and second arms 2534, 2554.

Alternatively, in the second position, the retaining member 2500 can directly contact the flange 2110 such that the retaining member proximal end 2502 and the flange surface 2112 are in direct contact with each other. Such interaction between the retaining member 2500 and the flange 2110 can occur when the length 2123 of the set of ridges 2122 is equal to the first portion length 2121 and the length 2125 of the second exterior surface 2116 is completely interrupted by the set of ridges 2122. The flange 2110 can prevent linear movement of the retaining member 2500 along the wire member second portion 2108.

In use, an external force is exerted against the temporary fixation device 2000 such that the external force is exerted against the wire member 2100 at the wire member proximal end 2102. The force is accomplished by exerting the force on the first exterior surface 2114 of the wire member 2100 in which the force is directed toward the wire member distal end 2104. As the tip 2118 and retaining member 2500 engage a patient's bone due to the force exerted on the wire member 2100, the retaining member 2500 moves linearly along the second portion 2108 toward the wire member proximal end 2102 opposite to the direction of the external force exerted on the wire member 2100. During the movement of the retaining member 2500 from its first position to its second position, each of the first and second arms 2534, 2554 transitions from its first position to its second position. Such transition allows the retaining member 2500 to constantly engage the set of ridges 2122 during movement such that the wire member 2100 and retaining member 2500 are attached by use of a mechanical mechanism (e.g., a ratcheting mechanism). Once the exerted force ceases and the temporary fixation device 2000 has met its desired depth within the patient's bone, the retaining member 2500 maintains its position on the wire member second portion 2108.

FIGS. 23 through 29 illustrate another temporary fixation device 3000. The temporary fixation device 3000 is similar to the temporary fixation device 1000 illustrated in FIGS. 1 through 6 and described above, except as detailed below. The temporary fixation device 3000 includes a wire member 3100, a retaining member 3500, and a spring member 3700.

Figure 27:
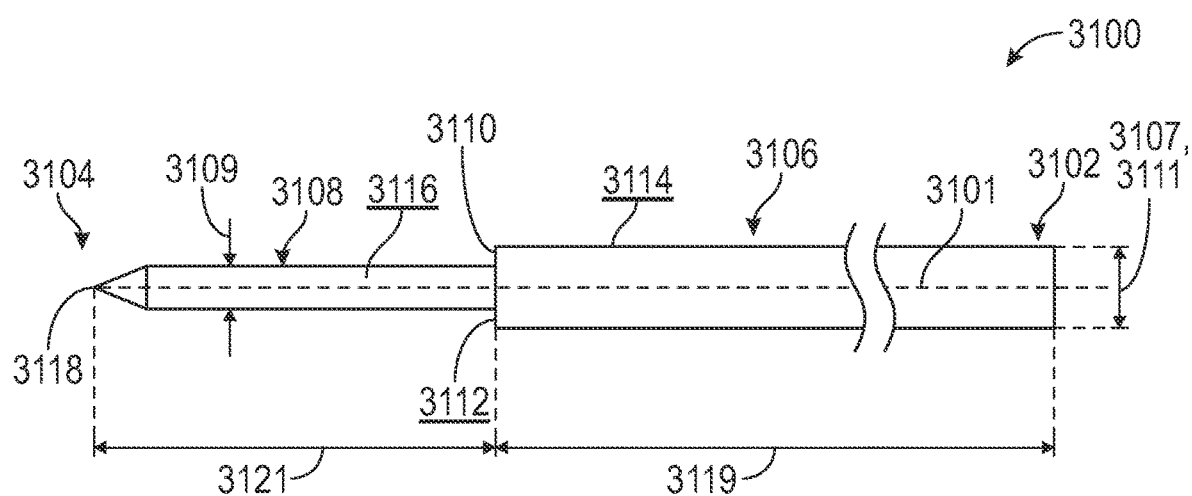
FIG. 27 is a side view of the wire member of the temporary fixation device illustrated in FIG. 23.

As illustrated in FIG. 27, the wire member 3100 has a wire member proximal end 3102, a wire member distal end 3104, a lengthwise axis 3101 that extends from the wire member proximal end 3102 to the wire member distal end 3104, a wire member first portion 3106 that defines a first outer diameter 3107, a first exterior surface 3114, and a first portion length 3119, a wire member second portion 3108 that defines a second outer diameter 3109, a second exterior surface 3116, and a second portion length 3121, a flange 3110 that defines a third outer diameter 3111 and a flange surface 3112, and a tip 3118 defined at the wire member distal end 3104. The wire member 3100 is made of a first material similar to the wire member 1100 of the temporary fixation device 1000 described above.

Figure 25:
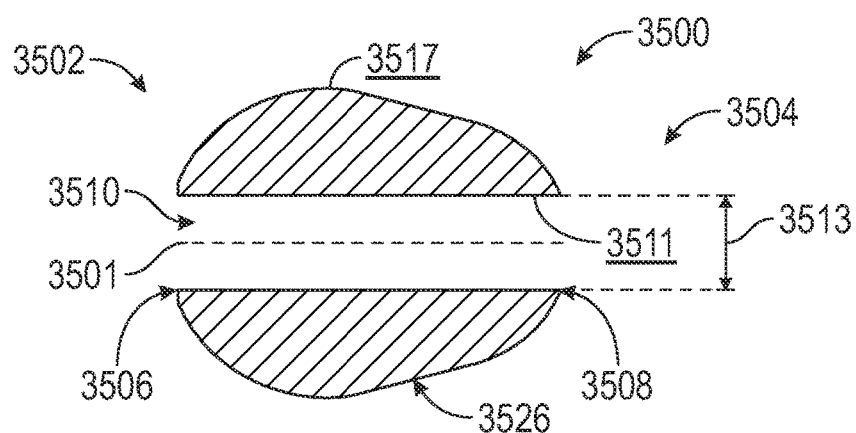
FIG. 25 is a cross-sectional view of the retaining member of the temporary fixation device illustrated in FIG. 23.

As illustrated in FIGS. 25 and 28, the retaining member 3500 has a retaining member proximal end 3502, a retaining member distal end 3504, a lengthwise axis 3501 that extends from the retaining member proximal end 3502 to the retaining member distal end 3504, a first opening 3506 defined at the retaining member proximal end 3502, a second opening 3508 defined at the retaining member distal end 3504, a passageway 3510 extending between the first and second openings 3506, 3508, an interior surface 3511 disposed within the passageway 3510, a first inner diameter 3513 defined by the first opening 3506, the second opening 3508, and the passageway 3510, a second inner diameter 3515 defined by the first opening 3506, the second opening 3508, and the passageway 3510, an exterior surface 3517 that extends from the retaining member proximal end 3502 to the retaining member distal end 3504, and a distal end portion 3526 that extends from the retaining member distal end 3504 toward the retaining member proximal end 3502 and defines a rounded-shape. The retaining member 3500 has a tapered-shape such that a portion of the retaining member 3500 that extends from the retaining member distal end 3504 toward the retaining member proximal end 3502 defines a greater diameter than a portion of the retaining 3500 that extends from the retaining member proximal end 3502 toward the retaining member distal end 3504. The retaining member 3500 is made of a second material similar to the retaining member 1500 of the temporary fixation device 1000 described above. The retaining member 3500 is moveable between a first position, as shown in FIGS. 23 and 28, and a second position, as shown in FIG. 29.

Figure 26:
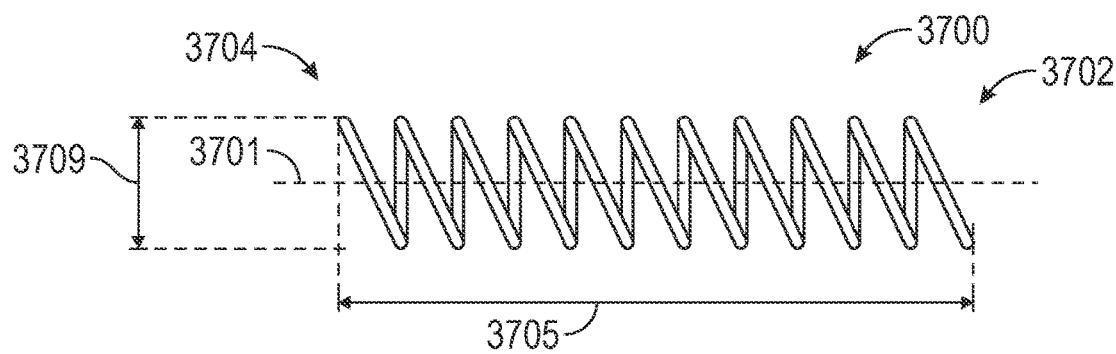
FIG. 26 is a side view of the spring member of the temporary fixation device illustrated in FIG. 23.

As illustrated in FIGS. 26, 28, and 29, the spring member 3700 has a spring member proximal end 3702, a spring member distal end 3704, a lengthwise axis 3701 that extends from the spring member proximal end 3702 to the spring member distal end 3704, a spring first length 3705, a spring second length 3707, and a spring diameter 3709. The spring member 3700 is moveable between a first position, as shown in FIGS. 23 and 28, and a second position, as shown in FIG. 29. The spring member 3700 is a compression-type spring such that the spring member 3700 is biased to its first position defined by the spring first length 3705.

In the illustrated embodiment, the spring member 3700 is disposed between the retaining member 3500 and the flange 3110 and is free of connection from the retaining member 3500 and the flange 3110. The spring member 3700 interacts with and directly contacts the retaining member 3500 such that the spring member distal end 3704 interacts with and directly contacts the retaining member proximal end 3502. The spring member 3700 also interacts with and directly contacts the wire member 3100 such that the spring member proximal end 3702 interacts with and directly contacts the flange 3110. Each of the spring first and second lengths 3705, 3707 measures the distance between the spring member proximal end 3702 and the spring member distal end 3704. The spring first length 3705 is defined when the spring member 3700 is in the first position. The spring second length 3707 is defined when the spring member 3700 is in the second position. The spring first length 3705 is greater than the spring second length 3707. The spring diameter 3709 is less than the first and third outer diameters 3107, 3111 and is greater than the second outer diameter 3109. Alternatively, the spring diameter 3709 can be greater than the first outer diameter 3107 and/or greater than the third outer diameter 3111.

While the spring member 3700 is free of connection from the retaining member 3500 and the wire member 3100 for the temporary fixation device 3000, a temporary fixation device can have any suitable structural attachment and/or interaction between a spring member, a wire member, and a retaining member. Selection of a suitable structural attachment and/or interaction between a spring member, a wire member, and a retaining member can be based on various considerations, including the size, shape, and configuration of a spring member, a wire member, and a retaining member, the desired force exerted against a retaining member and/or a wire member by a spring member, and other considerations. Examples of suitable structural attachments and/or interactions include a spring member attaching to a retaining member and a wire member, a spring member attaching to a retaining member and directly contacting a wire member, a spring member directly contacting a retaining member and attaching to a wire member, a spring member directly contacting a retaining member and a wire member, and any other structural attachments and/or interactions between a spring member, a wire member, and a retaining member suitable for a particular embodiment.

While the spring member 3700 has been described and illustrated as being a compression-type spring such that the spring member 3700 is biased to its first position, any suitable type of spring can be used for a spring member. Selection of a suitable type of spring can be based on various consideration, including the desired interaction between a retaining member, a wire member, and a spring member. Examples of suitable types of springs for a spring member include a compression spring, an extension spring, a torsion spring, a linear rate spring, a variable rate spring, a constant force spring, a Belleville spring, a drawbar spring, a volute spring, a flat spring, and any other types of springs for a spring member suitable for a particular embodiment.

FIG. 28 illustrates the temporary fixation device 3000 in a first configuration, and FIG. 29 illustrates the temporary fixation device 3000 in a second configuration.

When the temporary fixation device 3000 is in the first configuration, each of the retaining member 3500 and the spring member 3700 is in its first position. Prior to the retaining member 3500 engaging the wire member second portion 3108, the retaining member defines the first inner diameter 3513 similar to that of the retaining member 1500 of the temporary fixation device 1000 illustrated above. In the first position, the retaining member 3500 is positioned along a portion of the wire member second portion 3108 closer to wire member distal end 3104. The tip 3118 is disposed distal to the retaining member second opening 3508. The interior surface 3511 of the retaining member 3500 and the second exterior surface 3116 of the second portion 3108 are in direct contact with each other along the entire retaining member 3500 and a portion of the wire member second portion 3108. The retaining member 3500 defines the second inner diameter 3515 in the first position. The second inner diameter 3515 is greater than the first inner diameter 3513 and the second outer diameter 3109. The transition of the retaining member 3500 between the first inner diameter 3513 and the second inner diameter 3515 creates a structural interface between the retaining member 3500 and the wire member 3100 (e.g., a friction fit) to militate against, but allow, movement of the retaining member 3500 along the wire member second portion 3108.

Alternatively, the friction fit between the retaining member 3500 and the wire member 3100 can be omitted such that the retaining member 3500 freely moves along the wire member 3100 and such resistance is between the retaining member 3500 and the spring member 3700. The spring member 3700 is in its first position such that the spring member 3700 defines the spring first length 3705. The spring member distal end 3704 is disposed closer to the tip 3118 and the wire member distal end 3104.

When the temporary fixation device 3000 is in the second configuration, each of the retaining member 3500 and the spring member 3700 is in its second position. In the second position, the retaining member 3500 is positioned along the wire member second portion 3108 closer to the flange 3110 and the wire member proximal end 3102. The retaining member 3500 defines the second inner diameter 3515 at its second position. The spring member 3700 is in its second position such that the spring member 3700 defines the second length 3707. The spring member distal end 3704 is disposed closer to the flange 3110 and the wire member proximal end 3102.

In use, an external force is exerted against the temporary fixation device 3000 such that the external force is exerted against the wire member 3100 at the wire member proximal end 3102. The force is accomplished by exerting the force on the first exterior surface 3114 in which the force is directed toward the wire member distal end 3104. As the tip 3118 and retaining member 3500 engage a patient's bone due to the force exerted on the wire member 3100, the retaining member 3500 and the spring member distal end 3704 cooperatively move linearly along the wire member second portion 3108 toward the wire member proximal end 3102 opposite to the direction of the external force exerted on the wire member 3100. Once the retaining member 3500 transitions from its first position to its second position, the retaining member 3500 is constantly engaging the wire member second portion 3108 such that the interior surface 3511 of the retaining member 3500 and the second exterior surface 3116 of the wire member second portion 3108 are interacting with and directly contacting each other due to a friction fit. Alternatively, the friction fit between the retaining member 3500 and wire member 3100 can be omitted from this embodiment.

During the movement of the retaining member 3500 from its first position to its second position, the spring member 3700 transitions from its first position to its second position. As the spring member 3700 transitions from the first position and the second position, the spring member 3700 is constantly applying a force against the retaining member 3500 at the retaining member proximal end 3502 in a direction toward the wire member distal end 3104. The spring member 3700 is applying an opposite force against the wire member 3100, specifically against the flange 3110, in a direction toward the wire member proximal end 3102. The mechanical mechanism between each of the wire member 3100, the retaining member 3500, and the spring member 3700 (e.g, a spring-loaded mechanism) allows the retaining member 3500 to constantly exert a force against the patient's bone to maintain the temporary fixation device 3000 in a desired position in the patient's bone. The spring member 3700 maintains its force against the retaining member 3500 at the retaining member proximal end 3502 due to the mechanical mechanism between the retaining member 3500 and the spring member 3700. The mechanical mechanism between the wire member 3100, the retaining member 3500, and the spring member 3700 allows the temporary fixation device 3000 to maintain its second configuration in the patient's bone.

Inclusion of the spring-loaded mechanism in temporary fixation devices according to embodiments of the invention is considered advantageous at least because the second configuration of the retaining member 3500 moves to the first configuration when the device is removed from the bone plate. Therefore, the temporary fixation device 3000 and its retaining member 3500 is automatically moved by the spring force to the first configuration and advantageously can be used a second or subsequent times.

FIGS. 30 through 37 illustrate a fixation system 4000. The fixation system 4000 includes a temporary fixation device 4050 and a bone plate 4800. The temporary fixation device 4050 is similar to the temporary fixation device 1000 illustrated in FIGS. 1 through 6 and described above, except as detailed below. The temporary fixation device 4050 includes a wire member 4100 and a retaining member 4500. It is noted that while the illustrated temporary fixation device 4050 is similar to temporary fixation device 1000, a temporary fixation device in a fixation system can include a wire member according to any embodiment of the invention and a retaining member according to any embodiment of the invention.

Figure 32:
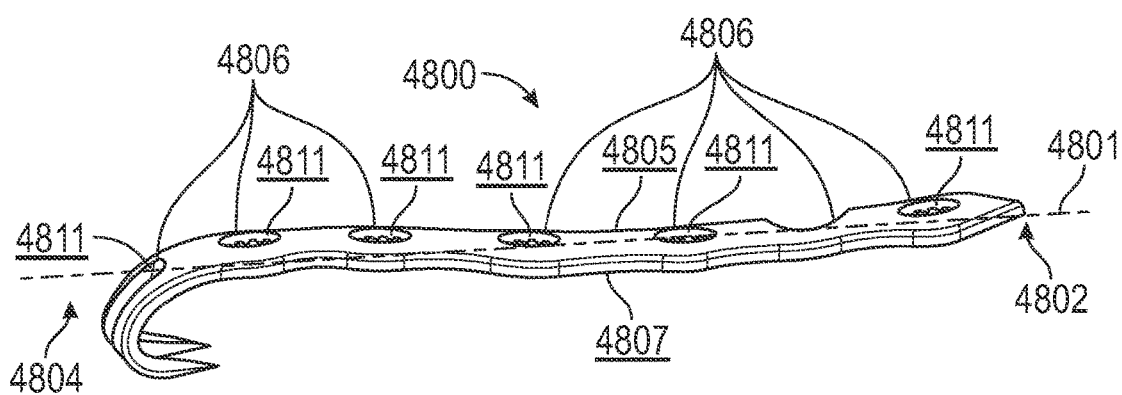
FIG. 32 is a side view of the bone plate of the fixation system illustrated in FIG. 30.

As illustrated in FIG. 32, the bone plate 4800 has a bone plate proximal end 4802, a bone plate distal end 4804, a lengthwise axis 4801 that extends from the bone plate proximal end 4802 to the bone plate distal end 4804, a first exterior surface 4805, a second exterior surface 4807, and a set of openings 4508. The first exterior surface 4805 engages the temporary fixation device 4050 and the second exterior surface 4805 engages a patient's bone during use, which is described in more detail below. The first and second exterior surfaces 4805, 4807 oppose each other. Each opening of the set of openings 4508 extends entirely through the bone plate 4800 from the first exterior surface 4505 to the second exterior surface 4507. Each opening of the set of openings 4508 is sized and configured to interact with and directly contact the retaining member 4500 of the temporary fixation device 4050, which is described in more detail below.

Figure 30:
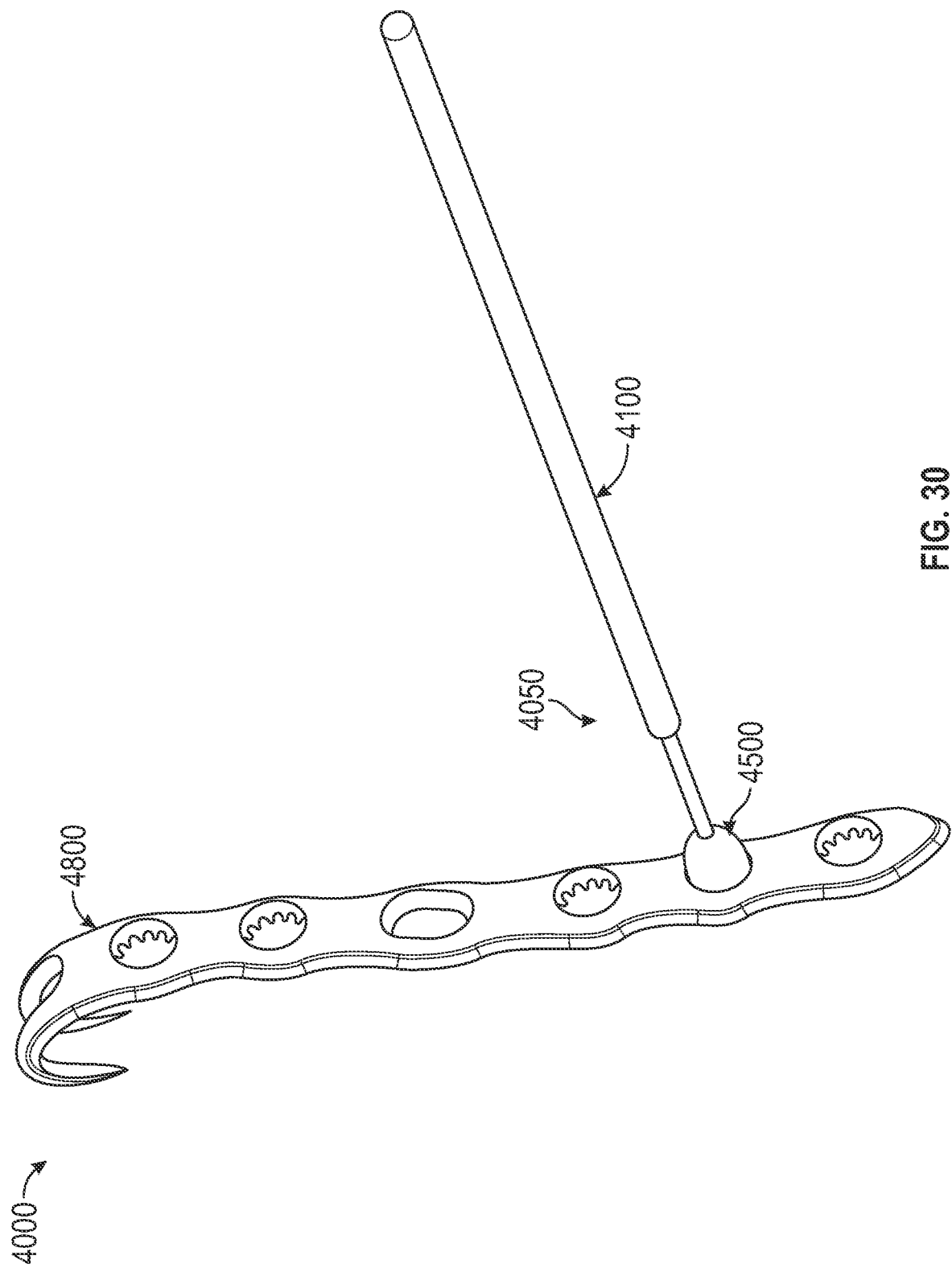
FIG. 30 is a perspective view of an example fixation system.
Figure 31:
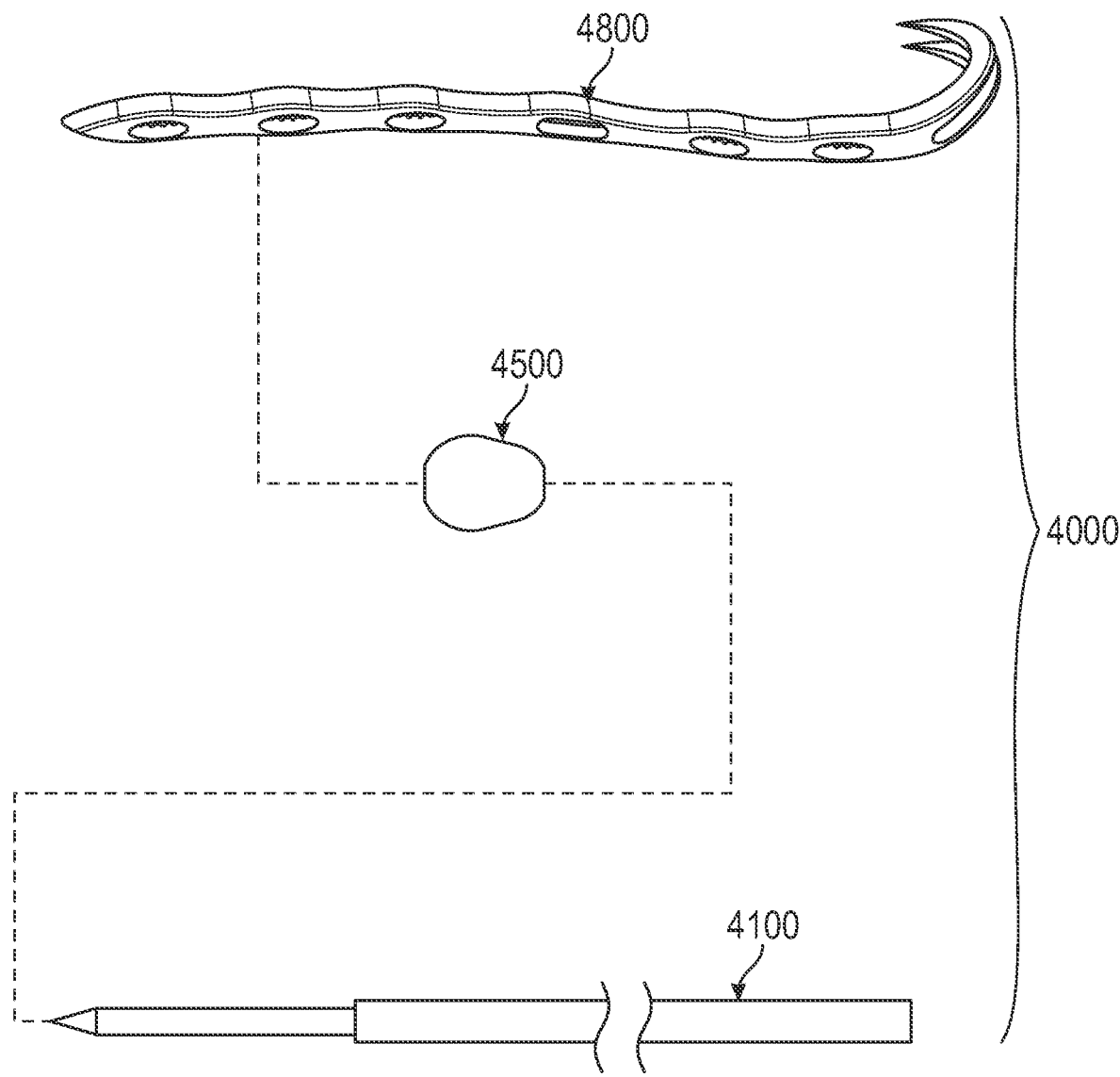
FIG. 31 is an exploded view of the fixation system illustrated in FIG. 30.
Figure 33:
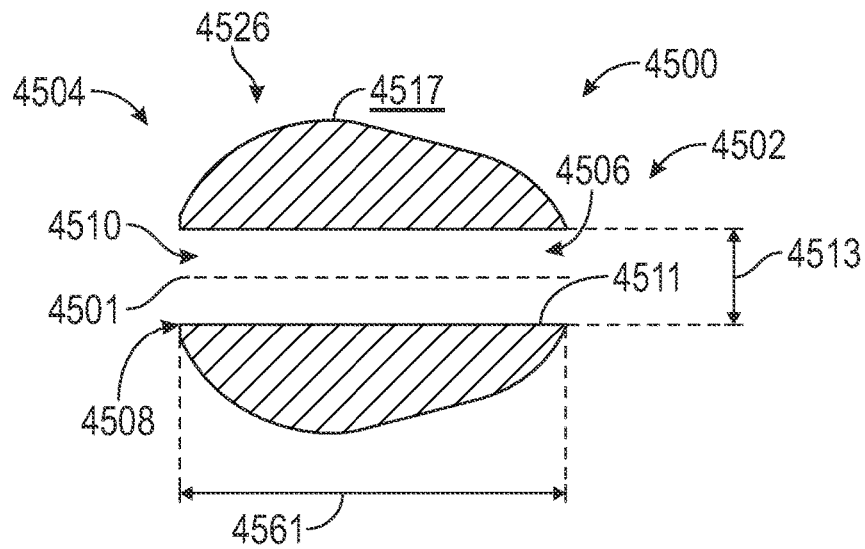
FIG. 33 is a cross-sectional view of the retaining member of the temporary fixation device of the fixation system illustrated in FIG. 30.
Figure 35:
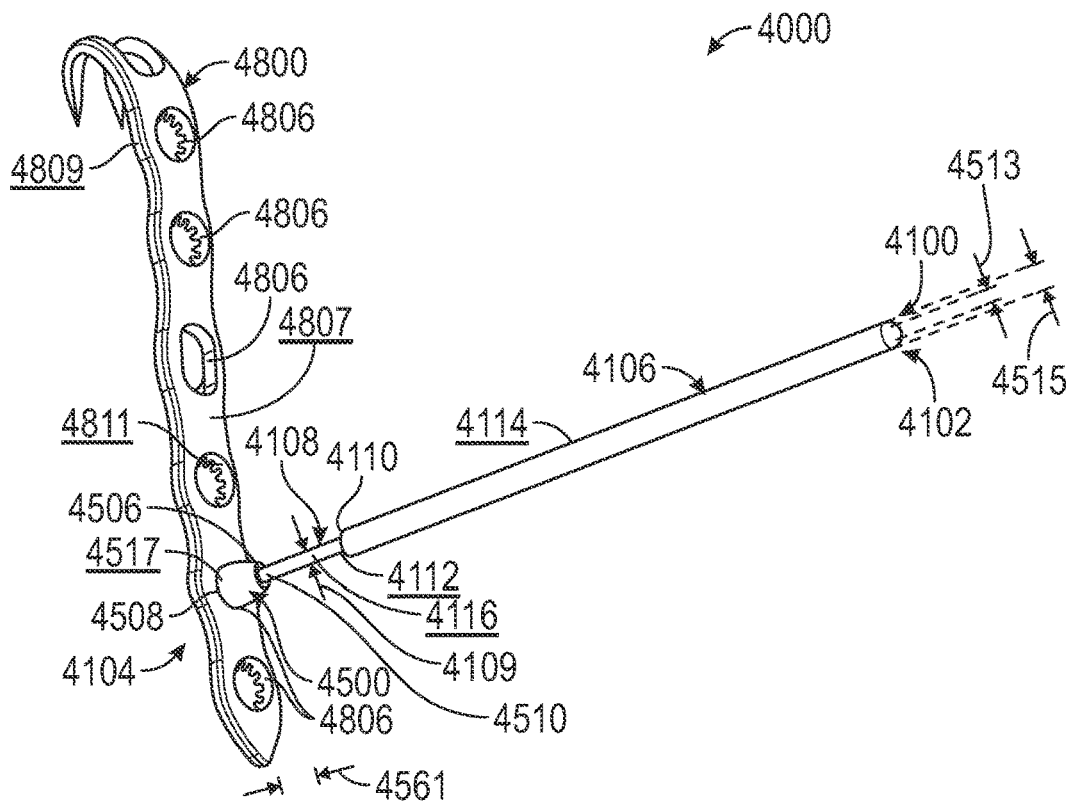
FIG. 35 is perspective view of the fixation system illustrated in FIG. 30. The temporary fixation device of the fixation system is shown in the first configuration.
Figure 36:
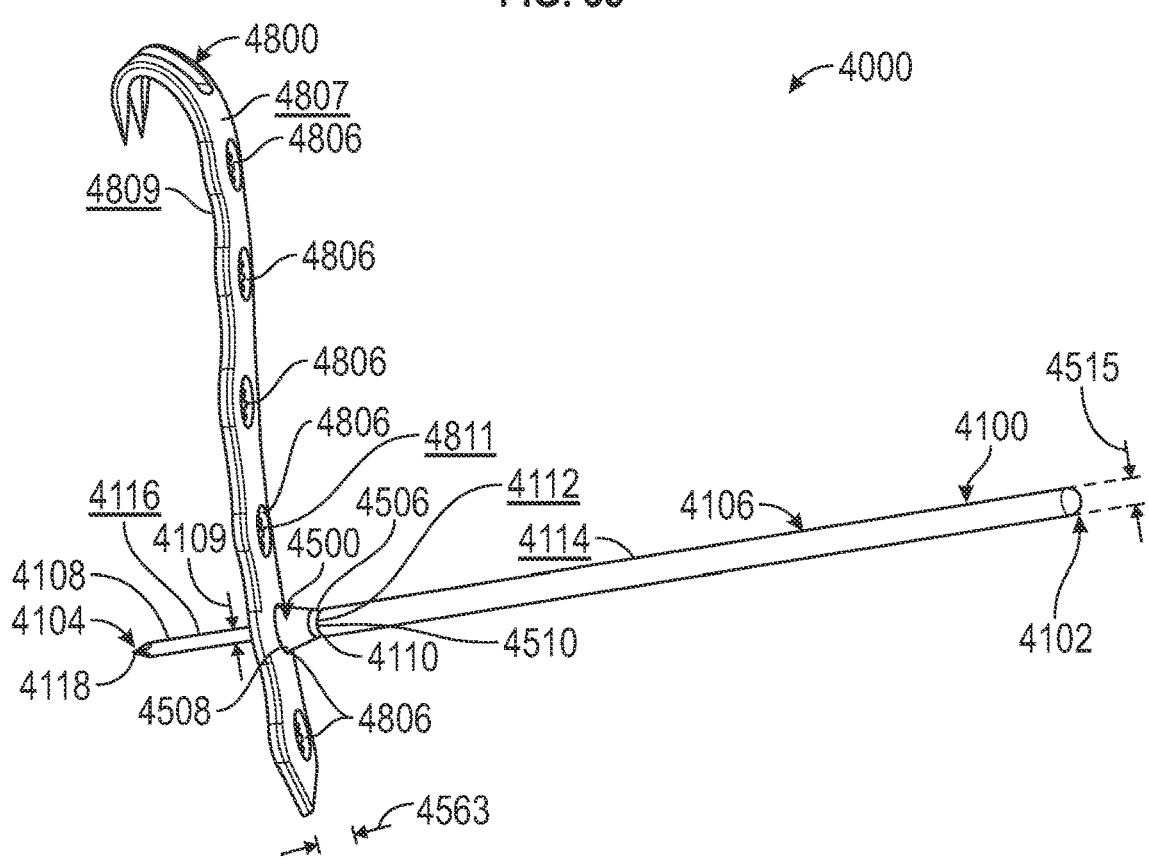
FIG. 36 is a perspective view of the fixation system illustrated in FIG. 30. The temporary fixation device of the fixation system is shown in the second configuration.

As illustrated in FIG. 33, the retaining member 4500 has a retaining member proximal end 4502, a retaining member distal end 4504, a lengthwise axis 4501 that extends from the retaining member proximal end 4502 to the retaining member distal end 4504, a first opening 4506 defined at the retaining member proximal end 4502, a second opening 4508 defined at the retaining member distal end 4504, a passageway 4510, an interior surface 4511, a first inner diameter 4513, a second inner diameter 4515, an exterior surface 4517, a distal end portion 4526, a retaining member first length 4561, and a retaining member second length 4563. The retaining member 4500 has a tapered-shape such that a portion of the retaining member 4500 that extends from the retaining member distal end 4504 toward the retaining member proximal end 4502 defines a greater diameter than a portion of the retaining 4500 that extends from the retaining member proximal end 4502 toward the retaining member distal end 4504. The retaining member 4500 is made of a second material similar to the retaining member 1500 of the temporary fixation device 1000 described above. The retaining member 4500 is moveable between a first position, as shown in FIGS. 30 and 35, and a second position, as shown in FIG. 36.

In the illustrated embodiment, each of the first and second openings 4506, 4508 provides access to the passageway 4510 such that the passageway 4510 has access to the exterior environment. The interior surface 4511 is disposed within the passageway 4510 and extends from the first opening 4506 to the second openings 4508. The exterior surface 4517 of the retaining member 4517 extends from the retaining member proximal end 4502 to the retaining member distal end 4504. Each of the first opening 4506, the second opening 4508, and the passageway 4510 defines the first inner diameter 4513 such that the first inner diameter 4513 is constant throughout the retaining member 4500. In the illustrated embodiment, the first inner diameter 4513 of the retaining member 4500 is less than second outer diameter 4109 of the wire member second portion 4108 prior to engaging the wire member second portion 4108. The second inner diameter 4515 of the retaining member 4515 is greater than the second outer diameter 4109 of the wire member second portion 4108 when engaging the wire member second portion 4108. The distal end portion 4526 extends from the retaining member distal end 4504 toward the retaining member proximal end 4502 and defines a rounded-shape. The distal end portion 4526 is sized and configured to engage an opening of the set of openings 4806 of the bone plate 4800 during use, which is described in more detail below. Each of the retaining member first length 4561 and retaining member second length 4563 is measured from the retaining member proximal end 4502 to the retaining member distal end 4504. The retaining member 4500 defines the retaining member first length 4561 when the temporary fixation device 4050 is in the first configuration, which is described in more detail below. The retaining member 4500 defines the retaining member second length 4563 when the temporary fixation device 4050 is in the second configuration, which is described in more detail below. The retaining member first length 4561 is greater than the retaining member second length 4563.

Figure 34:
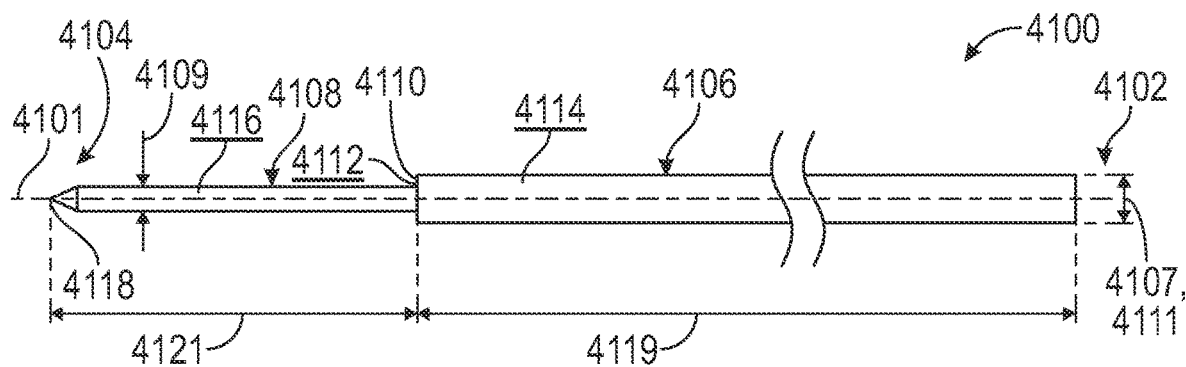
FIG. 34 is a side view of the wire member of the temporary fixation device of the fixation system illustrated in FIG. 30.

As illustrated in FIG. 34, the wire member 4100 has a wire member proximal end 4102, a wire member distal end 4104, a lengthwise axis 4101 that extends from the wire member proximal end 4102 to the wire member distal end 4104, a wire member first portion 4106 that defines a first outer diameter 4107, a first exterior surface 4114, and a first portion length 4119, a wire member second portion 4108 that defines a second outer diameter 4109, a second exterior surface 4116, and a second portion length 4121, a flange 4110 that defines a third outer diameter 4111 and a flange surface 4112, and a tip 4118 defined at the wire member distal end 4104. The wire member 4100 is made of a first material.

In the illustrated embodiment, the wire member first portion 4106 extends from the wire member proximal end 4102 toward the wire member distal end 4104. The wire member second portion 4108 extends from the wire member distal end 4104 toward the wire member proximal end 4102. In the illustrated embodiment, the first portion length 4119 is greater than the second portion length 4121 and the first outer diameter 4107 is greater than the second outer diameter 4109. The flange 4110 is disposed between the wire member proximal end 4102 and the wire member distal end 4104 and extends radially outward from the wire member 4100. In the illustrated embodiment, the third outer diameter 4111 is greater than the second outer diameter 4109 and is equal to the first outer diameter 4107. The flange surface 4112 faces towards the wire member distal end 4104 and is configured to engage the retaining member 4500, which is described in more detail below. The structural interface between the flange 4110 on the wire member 4100 is considered advantageous at least because the flange 4110 limits linear movement of the retaining member 4500 along the wire member second portion 4108 when the retaining member 4500 directly contacts the flange 4110, which is described in more detail below.

Figure 37A:
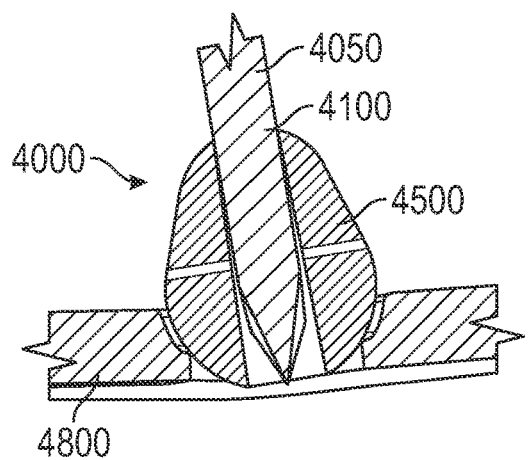
FIG. 37A is a schematic illustration of the fixation system illustrated in FIG. 30 in a first stage of use.
Figure 37B:
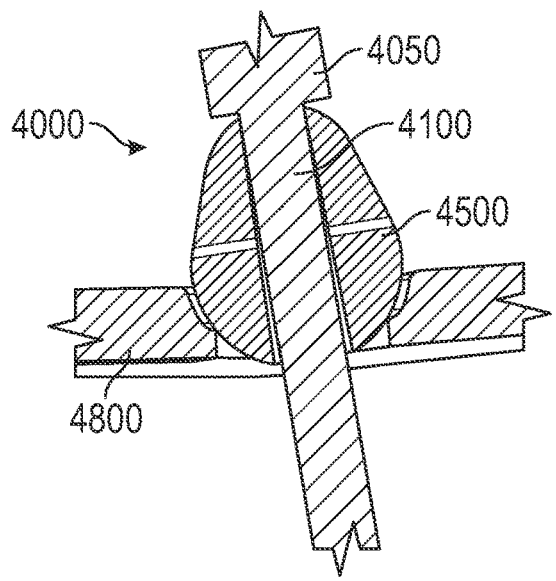
FIG. 37B is a schematic illustration of the fixation system illustrated in FIG. 30 in a second stage of use.
Figure 37C:
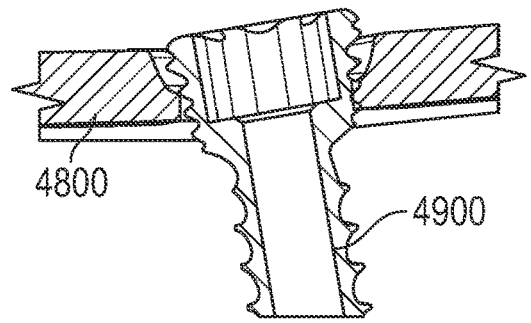
FIG. 37C is a schematic illustration of the bone plate of the fixation system illustrated in FIG. 30 after being secured to a bone with a screw. The temporary fixation device of the fixation system has been removed.

FIG. 35 illustrates the temporary fixation device 4050 in a first configuration, and FIG. 36 illustrates the temporary fixation device 4050 in a second configuration. FIG. 37A illustrates the temporary fixation device 4050 in the first configuration, and FIG. 37B illustrates the temporary fixation device 4050 in the second configuration. FIG. 37C illustrates the bone plate of the fixation system illustrated in FIG. 30 after being secured to a bone with a screw 4900. The temporary fixation device of the fixation system has been removed.

Prior to the retaining member 4500 engaging the wire member second portion 4108, the first opening 4506, the second opening 4508, and the passageway 4510 cooperatively define the first inner diameter 4513. When the temporary fixation device 4050 is in the first configuration, the retaining member 4500 is in the first position. In the first position, the retaining member 4500 is positioned along a portion of the second portion 4108 that is closer the wire member distal end 1104 The tip 4118 and a portion of the wire member second portion 4108 pass through the first opening 4506 and are disposed within the passageway 4510. The interior surface 4511 of the retaining member 4500 and the second exterior surface 4116 of the wire member second portion 4108 are in direct contact with each other at the retaining member first opening 4506 and along a portion of the second portion 4108 closer to the wire member distal end 4104. In the first position, the first opening 4506 and a portion of the passageway 4510 measured from the first opening 4506 to a location between the first opening 4507 and the second opening 4508 defines the second inner diameter 4515. The second opening 4508 and a portion of the passageway 4510 measured from the second opening 4508 to a location between the first opening 4506 and the second opening 4508 cooperatively define the first inner diameter 4513. The second inner diameter 4515 is greater than the first inner diameter 4513 and the second outer diameter 4109. As the temporary fixation device 4050 is introduced to the bone plate 4800, the exterior surface 4517 of the retaining member 4500 at the retaining member distal end 4504 interacts with and directly contacts the first exterior surface 4807 of the bone plate 4800 and/or the interior surface 4811 at an opening of the set of openings 4806. The retaining member 4500 defines the retaining member first length 4561 in the first position.

When the temporary fixation device 4000 is in the second configuration, the retaining member 4500 is in the second position. In the second position, the retaining member 4500 is disposed at a location between the wire member proximal end 4102 and the wire member distal end 4104 along the wire member second portion 4108 closer to the flange 4110. The retaining member 4500 is directly contacting the flange 4110 such that the exterior surface 4517 of the retaining member 4500 at the retaining member proximal end 4502 and the flange surface 4112 are in direct contact with each other. The flange 4110 prevents linear movement of the retaining member 4500 along the wire member second portion 4108. The interior surface 4511 of the retaining member 4500 and the second exterior surface 4116 of the wire member second portion 4108 are in direct contact with each other along the entire retaining member 4500 and a portion of the wire member second portion 4108. Each of the first opening 4506, the second opening 4508, and the passageway 4510 defines the second inner diameter 4515 when the retaining member 4500 reaches its second position. The tip 4118 and a portion of the wire member second portion 4108 measured from the wire member distal end 4104 to a location between the wire member distal end 4104 and the flange 4110 pass through an opening of the set of openings 4806 and are disposed distal to the second exterior surface 4809 of the bone plate 4800. The retaining member 4500 defines the retaining member second length 4563 when the bone plate 4800 and the flange 4110 cooperatively compress the retaining member 4500.

In use, an external force is exerted against the temporary fixation device 4000 such that the external force is exerted against the wire member 4100 at the wire member proximal end 4102. The force is exerted on the first exterior surface 4114 and directed toward the wire member distal end 4104. As the tip 4118 engages a patient's bone and the retaining member 4500 interacts with and directly contacts the bone plate 4800, the retaining member 4500 moves linearly along the wire member second portion 4108 toward the wire member proximal end 4102 opposite to the direction of the external force exerted on the wire member 4100. During the movement of the retaining member 4500 from its first position to its second position, each of the first opening 4506, the second opening 4508, and the passageway 4510 defines the second inner diameter 4515. The transition between the first inner diameter 4513 to the second inner diameter 4515 allows the retaining member 4500 to constantly engage the wire member second portion 4108 during movement such that the wire member 4100 and retaining member 4500 are frictionally fit to each other.

As the retaining member 4500 transitions from its first position to its second position, a portion of the exterior surface 4517 of the retaining member 4500 measured from the retaining member distal end 4504 to a location between the retaining member proximal end 4502 and the retaining member distal end 4504 interacts with and directly contacts the first exterior surface 4807 of the bone plate 4800 and/or the interior surface 4811 at an opening of the set of openings 4806. The shape of the retaining member 4500 is sized and configured to engage any opening of the set of openings 4806 so that the retaining member 4500 can constantly engage the bone plate 4800 during movement. Due to the rounded nature of the distal end portion 4526 and the circular form of the openings 4806 in the bone plate 4800, the structural interface between the retaining member 4500 and the bone plate 4800 assures that the distal tip of the wire member 4100 is positioned in the center of an opening of the bone plate 4800 when the retaining member is disposed on the opening of the bone plate 4800. As a result of this interface, the distal tip of the wire member 4100 creates an initial opening in the patient's bone that is substantially centered relative to the opening of the set of openings 4806 no matter the angle at which the wire member 4100 is disposed relative to the bone plate 4800. This is considered advantageous at least because it facilitates centering of the opening in the bone that is created by the temporary fixation device 4000 while allowing subsequent bone screws to be advanced into those openings in the bone at any desired angle, all while avoiding "jumping" or shifting of the plate on the bone as a result of off-centered alignment of the bone plate openings and the holes created in the bone.

The temporary fixation device 4000 meets its desired depth within the patient's bone once the exterior surface 4517 of the retaining member 4500 at the retaining member proximal end 4502 directly contacts the flange surface 4112 such that the flange 4110 prevents linear movement of the retaining member 4500. Once the exerted force ceases, the retaining member 4500 maintains its position on the wire member second portion 4108. The retaining member 4500 defines the retaining member second length 4563 in which the flange 4110 and the bone plate 4800 are cooperatively compressing the retaining member 4500 in its second position.

The structural interface between the retaining member 4500 and the bone plate 4800 of the fixation system 4000 is considered advantageous at least because a user, such as a surgeon, can drill a temporary fixation device into the patient's bone without the bone plate moving, shifting, and/or changing position during the drilling procedure. The structural interface between the retaining member 4500 and the bone plate 4800 allows the user to accurately drill a pilot hole and a temporary fixation device into the patient's bone that is substantially centered to an opening of a set of openings on a bone plate. Such accuracy allows a medical device, such as bone screw, to be simply disposed within the pilot hole to secure the bone plate to the patient's bone. The structural interface between the retaining member 4500 and the bone plate 4800 provides a quicker and more efficient procedure for temporarily attaching a bone plate to the patient's bone during a medical procedure. Furthermore, the shape of the retaining member 4500 is considered advantageous at least because the distal end portion 4126 is sized and configured to interact with and directly contact a bone plate 4800 for utilizing the structural interface between the retaining member 4500 and the bone plate 4800. The shape of the distal end portion 4126 allows the retaining member 4500 to engage the entire opening on a bone plate during the temporary attachment of a bone plate to a patient's bone. The shape of the distal end portion 4126 also allows a user to introduce the temporary attachment device 4050 at any suitable angle relative to an opening of the set of openings 4806 while the temporary fixation device 4000 remains substantially centered to the opening of the set of openings 4806.

While the fixation system 4000 includes the wire member 4100, the retaining member 4500, and the bone plate 4800, a fixation system can include any suitable wire member according to an embodiment, any suitable retaining member according to an embodiment, and any suitable bone plate according to an embodiment. Selection of suitable a wire member, a retaining member, and a bone plate for a fixation system can be based on various considerations, including the nature of a bone or bones with which the fixation system is intended to be used. Examples of wire members considered suitable for a fixation system include wire member 1100, wire member 1100', wire member 1100'', wire member 2100, wire member 3100, wire member 4100, and/or any other wire members considered suitable for a particular embodiment. Examples of retaining members considered suitable for a fixation system include retaining member 1500, retaining member 1500', retaining member 2500, retaining member 3500, retaining member 4500, and/or any other retaining members considered suitable for a particular embodiment. Examples of bone plates considered suitable for a fixation system include bone plate 4800 and/or other bone plates considered suitable for a particular embodiment.

FIG. 37 illustrates the fixation system 4000 associated with a packaging substrate 5010 to form a fixation kit 5000. The fixation kit 5000 comprises the wire member 4100, the retaining member 4500, the bone plate 4800, and an optional bone screw 4900. The wire member 4100 and the retaining member 4500 can be disposed in or on the packaging substrate as illustrated, as separate, unassembled components. Alternatively, the wire member 4100 and the retaining member can be disposed in or on the packaging substrate assembled together such that the tip 4118 and a portion of the wire member second portion 4108 measured from the tip 4118 to a location between the tip 4118 and the flange 4110 are disposed within the passageway 4510. If a bone screw is included in the fixation kit 5000, one or more than one bone screw 4900 can be included in the fixation kit 5000. The packaging substrate 5010 can be any suitable packaging material to package the fixation system 4000. Examples of suitable packaging containers for a packaging substrate include paperboard boxes, corrugated boxes, rigid boxes, chipboard boxes, shrink wrapping, sealable bags, polybags, backing material, and any other packaging container or substrate considered suitable for a particular embodiment.

Figure 38:
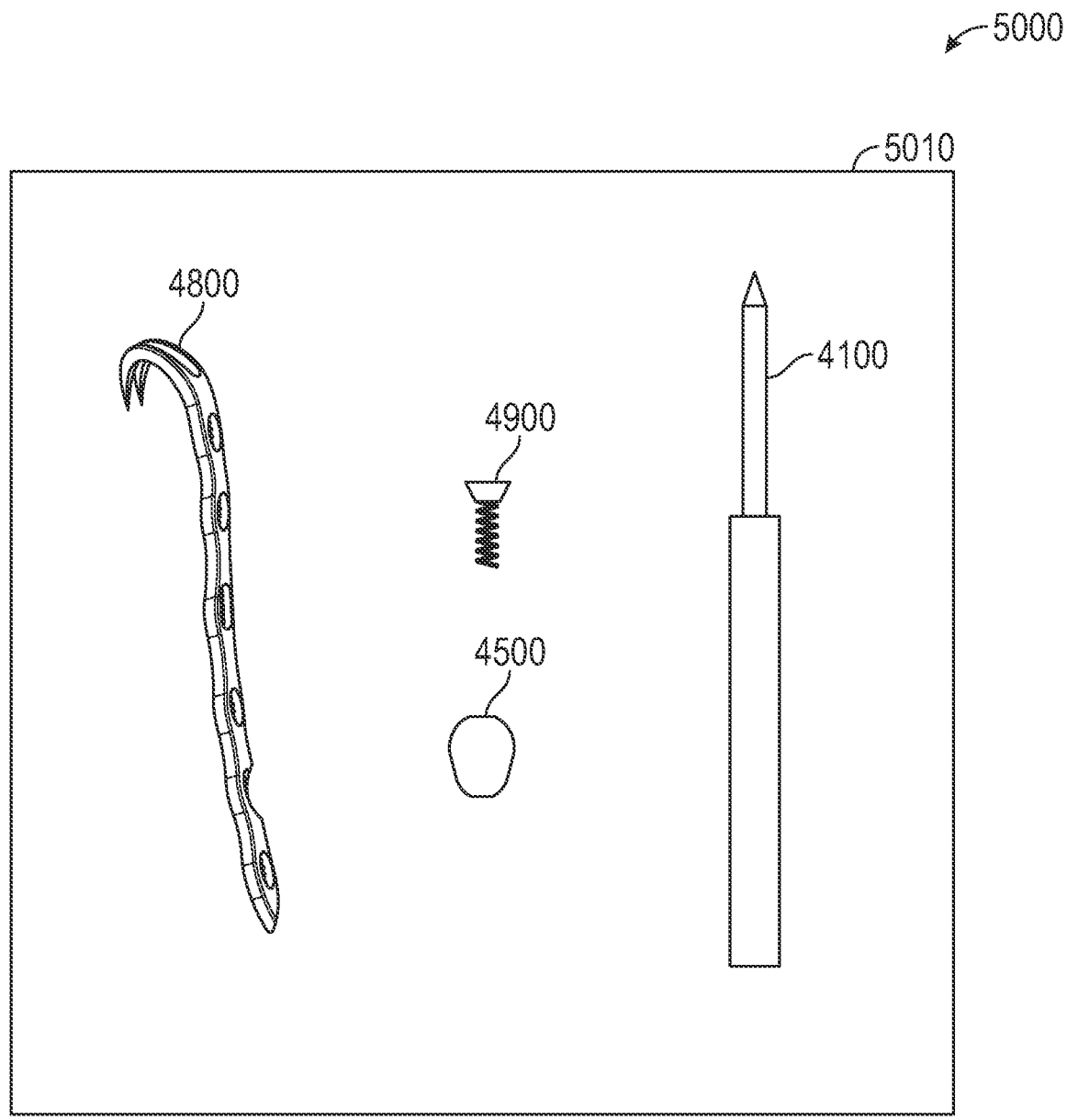
FIG. 38 is a schematic illustration of a fixation kit that includes the fixation system illustrated in FIG. 30.

FIG. 38 is a schematic illustration of an example method 6000 of fixing a bone plate to a patient's bone. Initial step 6002 comprises positioning a bone plate at a desired location on the patient's bone. Another step 6004 comprises positioning a temporary fixation device according to an embodiment on the bone plate such that the temporary fixation device is positioned in an opening of a set of openings on the bone plate. Another step 6006 comprises applying a force onto the wire member of the temporary fixation device to transition the temporary fixation device from a first configuration to a second configuration while the wire member of the temporary fixation device advances into the bone. This moves the retaining member of the temporary fixation device to the flange of the temporary fixation device, until the flange prevents further movement of the retaining member. At this point, the bone plate is temporarily fixed to the bone. If desired, another step 6008 comprising fixing the bone plate to the bone by passing a bone screw through an opening in the bone plate and into the bone can be included. If this step is included, the bone screw can be passed through a different opening in the bone plate or the same opening as the temporary fixation device. If the same opening is used, the temporary fixation device should be removed prior to passing the bone screw through the opening.

Step 6002 can be accomplished by using any suitable technique or method of positioning a bone plate on a patient's bone. The bone plate is positioned by applying force on the bone plate directed toward the patient's bone such that the bone plate is advanced into the patient at a desired location. Examples of bone plates considered suitable to complete step 6004 include bone plate 4800, variations of the bone plate described above, and any other bone plates considered suitable for a particular embodiment.

Step 6004 can be accomplished by applying a force on the temporary fixation device directed toward an opening of the set of openings on the bone plate until the temporary fixation device is directly contacting the bone plate. The force applied in step 6006 is accomplished once the exterior surface of the retaining member interacts with and directly contacts the first exterior surface of the bone plate and the interior surface of an opening of the step of openings of the bone plate. Examples of temporary fixation devices considered suitable to complete step 6006 include temporary fixation device 1000, temporary fixation device 2000, temporary fixation device 3000, temporary fixation device 4000, variations of the temporary fixation device described above, and any other temporary fixation devices considered suitable for a particular embodiment.

Step 6006 can be accomplished by applying a force on the wire member toward the bone plate. The force exerted in step 6008 is applied to the first exterior surface of the wire member and is directed toward the wire member distal end. The force applied in step 6008 can be both linear force on the wire member and rotation force on the wire member about the lengthwise axis of the wire member. The combination of linear force and rotational force on the wire member allows the tip of the wire member to bore a hole into the patient's bone to advance the wire member into the patient's bone and temporarily fix the bone plate to the patient's bone. The force applied on the wire member allows the temporary fixation device to transition from a first configuration to a second configuration, which is described above. The force applied on the wire member allows the retaining member of the temporary fixation device to transition from a first position to a second position, which is described above. The force applied in step 6008 can be accomplished by applying force on the wire member by a user (e.g., a driving tool), applying force on the wire member by a device (e.g., an electric drill), or any other application of force considered suitable for step 6008. Examples of wire members considered suitable to complete step 6008 include wire member 1100, wire member 1100', wire member 1100", wire member 2100, wire member 3100, wire member 4100, variations of the wire member described above, and any other wire members considered suitable for a particular embodiment. Examples of retaining members considered suitable to complete step 6008 include retaining member 1500, retaining member 1500', retaining member 2500, retaining member 3500, retaining member 4500, variations of the retaining member described above, and any other retaining members considered suitable for a particular embodiment.

Optionally, steps 6004 and 6006 can be repeated if an additional temporary fixation device is used to temporarily fix the bone to the patient's bone. The additional temporary fixation device can be introduced and positioned at a different opening on the bone plate to temporarily fix the bone plate at a different position along the patient's bone.

Step 6008 can be accomplished by fixing the bone plate to the bone by passing a bone screw through an opening in the bone plate and into the bone can be included. To accomplish step 6008, the bone screw can be passed through a different opening in the bone plate that is not occupied by the temporary fixation device to attach the bone plate to the patient's bone. The bone screw can also be passed through the same opening as the temporary fixation device only if the temporary fixation device is removed prior to passing the bone screw through the opening and attaching the bone plate to the patient's bone.

Figure 39:
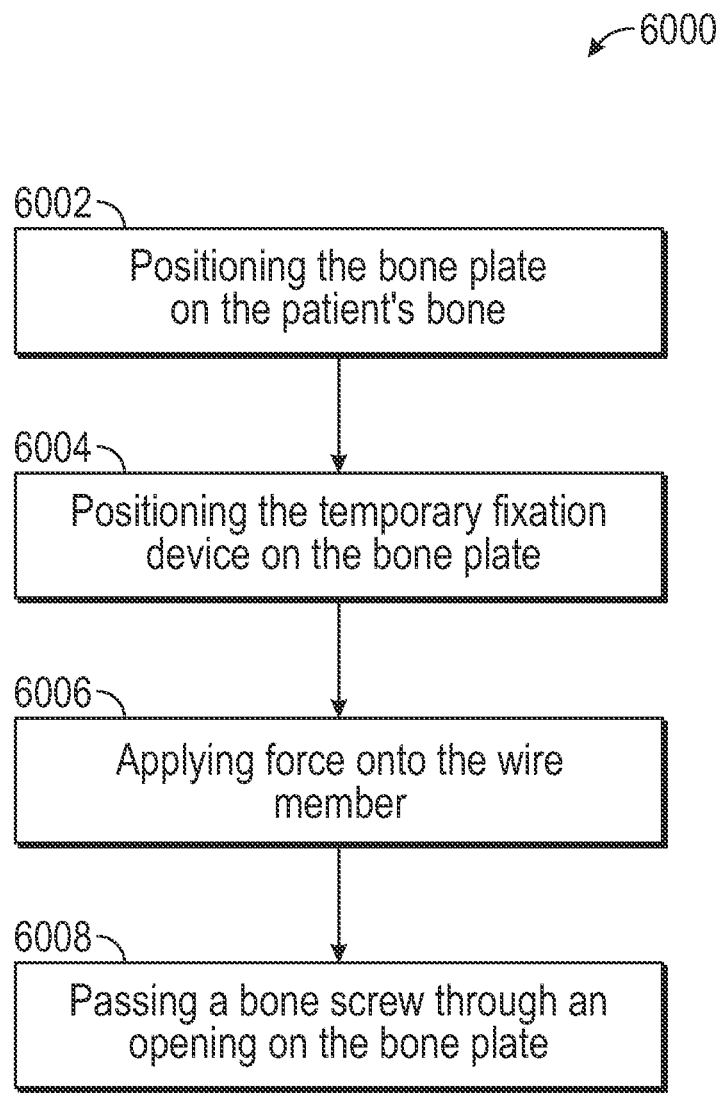
FIG. 39 is a schematic illustration of an example method of fixing a bone plate to a bone.
Figure 40:
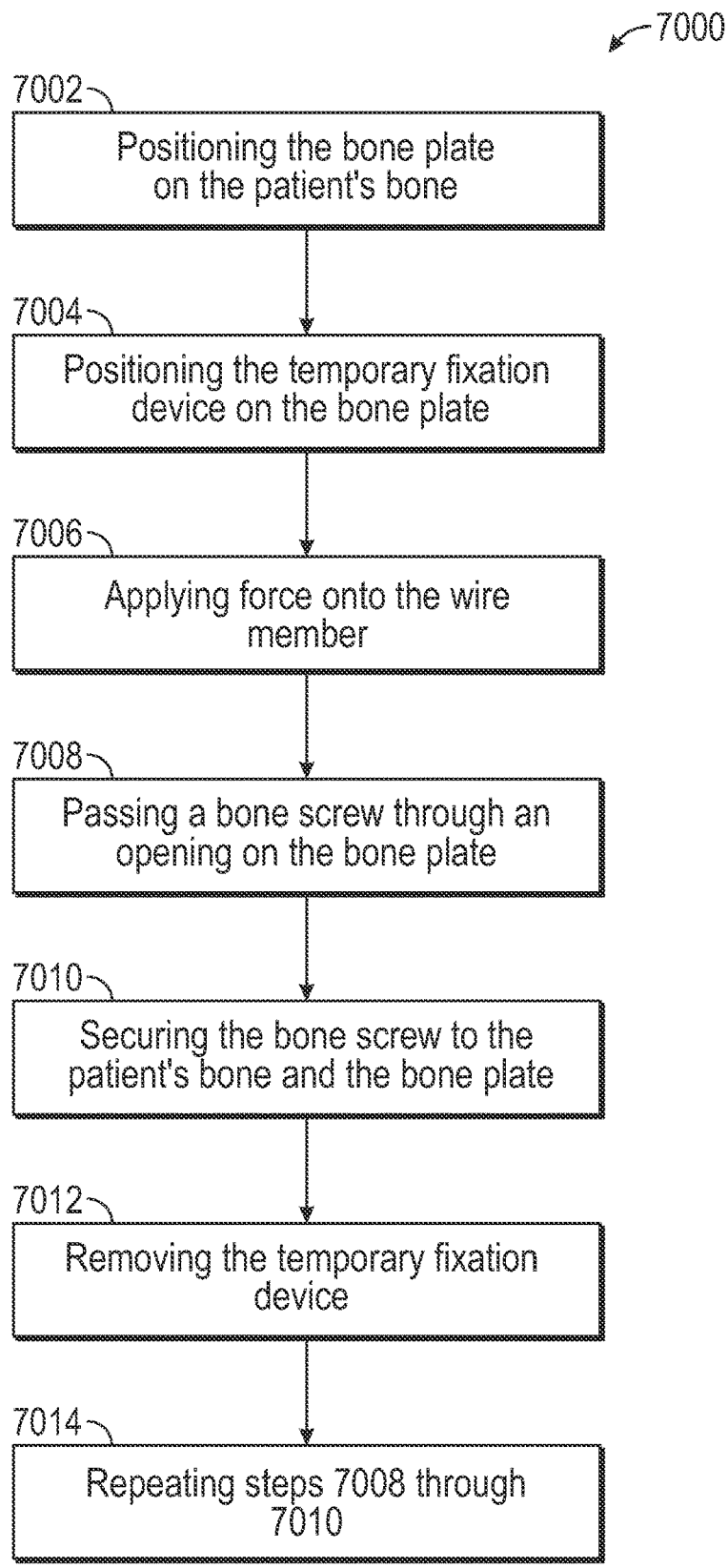
FIG. 40 is a schematic illustration of another example method of fixing a bone plate to a bone.

FIG. 39 is a schematic illustration of another example method 7000 of fixing a bone plate to a patient's bone. The initial step 7002 comprises positioning a bone plate at a desired location on the patient's bone. Another step 7004 comprises positioning a temporary fixation device on a bone plate such that the temporary fixation device is positioned in an opening of a set of openings on the bone plate. Another step 7006 comprises applying a force onto the wire member of the temporary fixation device to transition the temporary fixation device from a first configuration to a second configuration while the wire member of the temporary fixation device advances into the bone. At this point, the bone plate is temporarily fixed to the bone. If desired, another step 7008 comprising fixing the bone plate to the patient's bone by passing a bone screw through an opening in the bone plate and into the bone can be included. If this step is included, the bone screw can be passed through a different opening in the bone plate or the same opening as the temporary fixation device. If the same opening is used, the temporary fixation device should be removed prior to passing the bone screw through the opening. Another step 7010 comprises securing the bone screw into the patient's bone and attaching the bone plate to the patient's bone. Another step 7012 comprises removing the temporary fixation device from the patient's bone and the bone plate. Another step 7014 comprises repeating steps 7008 through 7010.

Step 7002 can be accomplished by using any suitable technique or method of positioning a bone plate on a patient's bone. The bone plate is positioned by applying force on the bone plate directed toward the patient's bone such that the bone plate is advanced into the patient at a desired location. Examples of bone plates considered suitable to complete step 7004 include bone plate 4800, variations of the bone plate described above, and any other bone plates considered suitable for a particular embodiment.

Step 7004 can be accomplished by applying a force on the temporary fixation device directed toward an opening of the set of openings on the bone plate until the temporary fixation device is directly contacting the bone plate. The force applied in step 7006 is accomplished once the exterior surface of the retaining member interacts with and directly contacts the first exterior surface of the bone plate and the interior surface of an opening of the step of openings of the bone plate. Examples of temporary fixation devices considered suitable to complete step 7006 include temporary fixation device 1000, temporary fixation device 2000, temporary fixation device 3000, temporary fixation device 4000, variations of the temporary fixation device described above, and any other temporary fixation devices considered suitable for a particular embodiment.

Step 7006 can be accomplished by applying a force on the wire member toward the bone plate. The force exerted in step 7008 is applied to the first exterior surface of the wire member and is directed toward the wire member distal end. The force applied in step 7008 can be both linear force on the wire member and rotation force on the wire member about the lengthwise axis of the wire member. The combination of linear force and rotational force on the wire member allows the tip of the wire member to bore a hole into the patient's bone to advance the wire member into the patient's bone and temporarily fix the bone plate to the patient's bone. The force applied on the wire member allows the temporary fixation device to transition from a first configuration to a second configuration, which is described above. The force applied on the wire member allows the retaining member of the temporary fixation device to transition from a first position to a second position, which is described above. The force applied in step 7008 can be accomplished by applying force on the wire member by a user (e.g., a driving tool), applying force on the wire member by a device (e.g., an electric drill), or any other application of force considered suitable for step 7008. Examples of wire members considered suitable to complete step 7008 include wire member 1100, wire member 1100', wire member 1100", wire member 2100, wire member 3100, wire member 4100, variations of the wire members described above, and any other wire members considered suitable for a particular embodiment. Examples of retaining members considered suitable to complete step 6008 include retaining member 1500, retaining member 1500', retaining member 2500, retaining member 3500, retaining member 4500, variations of the retaining members described above, and any other retaining member considered suitable for a particular embodiment.

Optionally, steps 7004 and 7006 can be repeated if additional temporary fixation devices are used to temporarily fix the bone plate to the patient's bone. The additional temporary fixation devices can be introduced and positioned at different openings on the bone plate to temporarily fix the bone plate at different positions along the patient's bone.

Step 7008 can be accomplished by fixing the bone plate to the bone by passing a bone screw through an opening in the bone plate and into the bone can be included. To accomplish step 7008, the bone screw can be passed through a different opening in the bone plate that is not occupied by the temporary fixation device to attach the bone plate to the patient's bone. The bone screw can also be passed through the same opening as the temporary fixation device only if the temporary fixation device is removed prior to passing the bone screw through the opening and attaching the bone plate to the patient's bone.

Step 7010 can be accomplished by applying a force on the bone screw toward the bone plate and into the patient's bone. The force exerted in step 7016 is applied at the proximal end of the bone screw and is directed toward the bone plate. The force applied in step 7016 can be both linear force on the bone screw and rotation force on the bone screw about the lengthwise axis of the bone screw. The combination of linear force and rotational force on the bone screw allows the tip of the bone screw to bore a hole into the patient's bone to advance the bone screw into the patient's bone and attach the bone plate to the patient's bone. The force applied in step 7016 can be accomplished by applying force on the bone screw by a user (e.g., a driving tool), applying force on the bone screw by a device (e.g., an electric drill), or any other application of force considered suitable for step 7016. Once the desired depth is reached, the exterior surface of the bone screw directly contacts the first exterior surface of the bone plate to secure the bone plate to the patient's bone. Optionally, the exterior surface of the bone screw can directly contact the interior surface of the opening on the bone plate to secure the bone plate to the patient's bone.

Optionally, step 7010 can be repeated if additional bone screws are used to attach the bone plate to the patient's bone. The additional bone screws can be introduced and positioned at different openings on the bone plate to attach the bone plate at different positions along the patient's bone.

Step 7012 can be accomplished by applying a force on the wire member away from the bone plate and the patient's bone. The force exerted in step 7018 is applied to the first exterior surface of the wire member and is directed away from the wire member distal end. The force applied in step 7018 can be linear force on the wire member and rotation force on the wire member about the lengthwise axis of the wire member. The force exerted on the wire member removes the wire member from the patient's bone and the bone plate. The force applied on the wire member allows the temporary fixation device to transition from its second configuration to its first configuration. The force applied on the wire member also allows the retaining member of the temporary fixation device to transition from its second position to it first position to relieve the structural interface between the bone plate and the retaining member. The force applied in step 7018 can be accomplished by applying force on the wire member by a user (e.g., a driving tool), applying force on the wire member by a device (e.g., an electric drill), or any other application of force considered suitable for step 7018.

Step 7014 is accomplished by repeating steps 7008 through 7010 when additional bone screws are used to secure the bone plate at openings once occupied by the temporary fixation devices. Optionally, step 7014 can be omitted if a user determines that the openings of the bone plate previously occupied by the temporary fixation device do not require additional bone screws to attach the bone plate to the patient's bone.

The foregoing detailed description provides example embodiments of the invention and includes the best mode for practicing the invention. The description and illustration of embodiments is intended only to provide examples of the invention and not to limit the scope of the invention, or its protection, in any manner.

We claim:

1. A temporary fixation device, comprising:
a wire member having a proximal end, a distal end, a flange disposed between the proximal end and the distal end, a first portion extending from the proximal end to the flange and defining a first outer diameter, and a second portion extending from the distal end toward the flange and defining a second outer diameter and a second portion outer surface, the first outer diameter being greater than the second outer diameter; and
a retaining member having an inner surface that defines an inner passageway having a passageway diameter that is less than the first outer diameter, the retaining member disposed on the second portion of the wire member and movable between a first position and a second position on the second portion of the wire member;
wherein the distal end defines a pointed tip;
wherein the retaining member has a retaining member first end defining a first opening and a retaining member second end defining at least two extensions that cooperatively define a second opening;
the first opening defining a first opening inner diameter that is greater than the second outer diameter; and
the at least two extensions movable toward and away from each other such that the second opening has a second opening first inner diameter that is less than the second outer diameter and a second opening second inner diameter that is greater than the second outer diameter, and configured to engage the flange when the retaining member is in the second position to prevent linear movement of the retaining member and to maintain the retaining member at the second position.

2. The temporary fixation device of claim 1, wherein the second portion outer surface comprises a continuous smooth surface.

3. The temporary fixation device of claim 1, wherein the at least two extensions comprises four extensions.

4. The temporary fixation device of claim 1, wherein the retaining member comprises a resilient material.

5. The temporary fixation device of claim 1, wherein the second portion outer surface defines a series of ridges.

6. The temporary fixation device of claim 5, wherein the series of ridges comprises a thread.

7. The temporary fixation device of claim 1, wherein the wire member comprises a metal or a metal alloy; and
wherein the retaining member comprises a resilient material.

* * * * *